United States Patent
Moffat et al.

(10) Patent No.: US 12,239,844 B2
(45) Date of Patent: Mar. 4, 2025

(54) SYSTEMS AND METHODS FOR OPERATING PHOTOTHERAPY KIOSKS

(71) Applicant: BeneSol, Inc., Bainbridge Island, WA (US)

(72) Inventors: William Alexander Moffat, Bainbridge Island, WA (US); Sen Wen, Bainbridge Island, WA (US); Keith W. Kirkwood, Bainbridge Island, WA (US); Linda Cox Arnsdorf, Bainbridge Island, WA (US)

(73) Assignee: BENESOL, INC., Bainbridge Island, WA (US)

( * ) Notice: Subject to any disclaimer, the term of this patent is extended or adjusted under 35 U.S.C. 154(b) by 0 days.

(21) Appl. No.: 16/771,564

(22) PCT Filed: Dec. 13, 2018

(86) PCT No.: PCT/US2018/065542
§ 371 (c)(1),
(2) Date: Jun. 10, 2020

(87) PCT Pub. No.: WO2019/118777
PCT Pub. Date: Jun. 20, 2019

(65) Prior Publication Data
US 2020/0391049 A1 Dec. 17, 2020

Related U.S. Application Data

(60) Provisional application No. 62/613,745, filed on Jan. 4, 2018, provisional application No. 62/599,252, filed (Continued)

(51) Int. Cl.
*A61N 5/06* (2006.01)
*A61B 5/00* (2006.01)
(Continued)

(52) U.S. Cl.
CPC ............ *A61N 5/0616* (2013.01); *A61B 5/445* (2013.01); *G06F 3/048* (2013.01); *G06N 20/00* (2019.01);
(Continued)

(58) Field of Classification Search
CPC .......... A61N 5/0616; A61N 2005/0628; A61N 2005/0627; A61N 2005/0632;
(Continued)

(56) References Cited

U.S. PATENT DOCUMENTS

| 5,265,598 A | 11/1993 | Searfoss et al. |
| 5,531,664 A | 7/1996 | Adachi et al. |

(Continued)

FOREIGN PATENT DOCUMENTS

| CN | 101045177 | 10/2007 |
| CN | 101548895 | 10/2009 |

(Continued)

OTHER PUBLICATIONS

"Asahi Spectra Optical Filters," https://web.archive.org/web2010051608304/http://www.asahispectra.com/opticalfilters/uv_bandpass_filter.html; archive of website from 2010, 2 pages.
(Continued)

*Primary Examiner* — Carl H Layno
*Assistant Examiner* — Manolis Pahakis
(74) *Attorney, Agent, or Firm* — Perkins Coie LLP

(57) ABSTRACT

A phototherapy system can provide functions such as user account management, skin type evaluation, treatment parameter determinations and adjustments, treatment blocking or warnings for some hazard prevention, treatment education and guidance, session records access, treatment regime determination, scheduling, and converting treatment parameter determinations into kiosk controls. The phototherapy system functions can be performed based on user (Continued)

input, records of user data, guidelines and algorithms for treatment parameter selection, direct measurements, etc. These data sources can be accessed or implemented though one or more of: a phototherapy kiosk, a personal computing device, a server system, a third-party system, or any combination thereof. An interactive user interface can be used though any of these devices to facilitate user control and user feedback for the phototherapy system.

20 Claims, 11 Drawing Sheets

Related U.S. Application Data on Dec. 15, 2017, provisional application No. 62/599,242, filed on Dec. 15, 2017.

(51) Int. Cl.
*G06F 3/048* (2013.01)
*G06N 20/00* (2019.01)
*G16H 20/13* (2018.01)
*G16H 20/40* (2018.01)

(52) U.S. Cl.
CPC .............. *G16H 20/13* (2018.01); *G16H 20/40* (2018.01); *A61N 2005/0627* (2013.01); *A61N 2005/0628* (2013.01); *A61N 2005/0632* (2013.01); *A61N 2005/064* (2013.01); *A61N 2005/0661* (2013.01)

(58) Field of Classification Search
CPC ..... A61N 2005/064; A61N 2005/0661; G16H 20/40; G16H 20/13; G06N 20/00; A61B 5/445; G06F 3/048
See application file for complete search history.

(56) References Cited

U.S. PATENT DOCUMENTS

| | | | |
|---|---|---|---|
| 5,576,591 A | 11/1996 | Block et al. | |
| 6,402,774 B1 | 6/2002 | Caldironi | |
| 6,413,268 B1 | 7/2002 | Hartman | |
| 6,436,127 B1* | 8/2002 | Anderson | A61B 5/0071 128/898 |
| 6,567,999 B1 | 5/2003 | Thurner | |
| 7,638,780 B2 | 12/2009 | Kilburn et al. | |
| 8,647,373 B1 | 2/2014 | Shepherd et al. | |
| 10,226,641 B2 | 3/2019 | Moffat | |
| 2001/0003800 A1 | 6/2001 | Crowley | |
| 2003/0045916 A1* | 3/2003 | Anderson | A61B 5/0064 607/89 |
| 2003/0100935 A1 | 5/2003 | Kratz | |
| 2004/0138726 A1 | 7/2004 | Savage et al. | |
| 2004/0186082 A1 | 9/2004 | Hartman | |
| 2004/0225339 A1 | 11/2004 | Yaroslavsky et al. | |
| 2005/0015124 A1 | 1/2005 | Irwin | |
| 2005/0143793 A1 | 6/2005 | Korman et al. | |
| 2005/0148270 A1 | 7/2005 | Eden | |
| 2005/0261750 A1 | 11/2005 | McDaniel | |
| 2006/0106435 A1 | 5/2006 | Fraval | |
| 2006/0151709 A1 | 7/2006 | Hahl | |
| 2006/0206173 A1 | 9/2006 | Gertner et al. | |
| 2006/0217789 A1 | 9/2006 | Perez | |
| 2007/0208395 A1 | 9/2007 | Leclerc et al. | |
| 2007/0233210 A1 | 10/2007 | Morita et al. | |
| 2008/0103560 A1 | 5/2008 | Powell et al. | |
| 2008/0125834 A1* | 5/2008 | Hendrix | A61N 5/0616 607/88 |
| 2008/0172113 A1 | 7/2008 | Gourgouliatos et al. | |
| 2008/0211378 A1 | 9/2008 | Dutta et al. | |
| 2008/0224592 A1 | 9/2008 | Reich et al. | |
| 2008/0312721 A1 | 12/2008 | Lemieux | |
| 2009/0005839 A1 | 1/2009 | Griffith et al. | |
| 2009/0020711 A1 | 1/2009 | Hansmann et al. | |
| 2009/0093799 A1 | 4/2009 | Davenport et al. | |
| 2009/0118799 A1* | 5/2009 | Nanninga | A61N 5/0614 607/88 |
| 2009/0134345 A1 | 5/2009 | Gentry et al. | |
| 2010/0185064 A1* | 7/2010 | Bandic | A61B 5/415 600/306 |
| 2010/0241196 A1 | 9/2010 | Meyer | |
| 2010/0331929 A1 | 12/2010 | Burrows et al. | |
| 2011/0004280 A1 | 1/2011 | Irwin | |
| 2011/0212410 A1 | 9/2011 | Fiset | |
| 2011/0218595 A1 | 9/2011 | McMillan | |
| 2011/0299056 A1 | 12/2011 | Williamson et al. | |
| 2012/0071954 A1 | 3/2012 | Kao et al. | |
| 2012/0148976 A1 | 6/2012 | Brawn | |
| 2012/0282135 A1* | 11/2012 | Trapani | A61L 2/208 422/3 |
| 2013/0018442 A1 | 1/2013 | Irwin et al. | |
| 2013/0030264 A1* | 1/2013 | Gopalakrishnan | H05B 45/12 600/310 |
| 2013/0131762 A1* | 5/2013 | Oversluizen | A61N 5/0616 607/90 |
| 2013/0172963 A1 | 7/2013 | Moffat | |
| 2013/0245724 A1* | 9/2013 | Kaufman | A61N 5/06 607/88 |
| 2013/0253621 A1 | 9/2013 | DeLuca et al. | |
| 2013/0310730 A1 | 11/2013 | Goren et al. | |
| 2014/0074193 A1* | 3/2014 | Luzon | A61N 5/0616 607/88 |
| 2014/0121732 A1 | 5/2014 | Goren et al. | |
| 2014/0276248 A1* | 9/2014 | Hall | A61N 1/0432 604/20 |
| 2014/0277299 A1* | 9/2014 | Intintoli | A61N 5/0616 607/94 |
| 2015/0088231 A1 | 3/2015 | Rubinfeld | |
| 2015/0102208 A1 | 4/2015 | Appelboom et al. | |
| 2015/0165229 A1 | 6/2015 | Rodrigues | |
| 2015/0217130 A1 | 8/2015 | Gross et al. | |
| 2015/0217132 A1 | 8/2015 | Makkapati et al. | |
| 2015/0238774 A1 | 8/2015 | Anderson et al. | |
| 2016/0048826 A1* | 2/2016 | Fefferman | G06K 19/06131 705/23 |
| 2016/0129279 A1 | 5/2016 | Ferolito | |
| 2016/0303395 A1 | 10/2016 | Moffat | |
| 2016/0317686 A1* | 11/2016 | Dayton | A61L 2/10 |
| 2017/0056238 A1 | 3/2017 | Yi et al. | |
| 2017/0118854 A1* | 4/2017 | Dumont | H01R 13/15 |
| 2017/0225006 A1* | 8/2017 | Anderson | A61K 35/04 |
| 2018/0014777 A1 | 1/2018 | Amir et al. | |
| 2018/0056088 A1 | 3/2018 | Moffat | |
| 2018/0133503 A1 | 5/2018 | Moffat | |
| 2018/0206779 A1 | 7/2018 | Kono | |
| 2018/0353770 A1 | 12/2018 | Moffat | |
| 2018/0360709 A1 | 12/2018 | Rabe et al. | |
| 2018/0369604 A1* | 12/2018 | Gamelin | A61N 5/06 |
| 2019/0099613 A1 | 4/2019 | Estes et al. | |
| 2019/0133515 A1* | 5/2019 | Park | A61B 5/0064 |
| 2019/0160303 A1 | 5/2019 | Moffat, IV | |
| 2020/0030628 A1 | 1/2020 | Moffat et al. | |
| 2020/0212265 A1 | 7/2020 | Ho et al. | |
| 2020/0376292 A1 | 12/2020 | Moffat et al. | |
| 2021/0128939 A1* | 5/2021 | Verghese | A61N 5/0616 |
| 2021/0260402 A1 | 8/2021 | Moffat et al. | |
| 2022/0249863 A1 | 8/2022 | Moffat et al. | |

FOREIGN PATENT DOCUMENTS

| | | |
|---|---|---|
| CN | 201871131 | 6/2011 |
| CN | 104168953 | 7/2013 |
| CN | 107427688 | 8/2016 |
| CN | 106573155 | 4/2017 |
| DE | 7623367 | 2/1977 |
| DE | 3126236 | 1/1983 |
| DE | 9000705 | 3/1990 |
| DE | 19622074 A1 | 12/1997 |
| DE | 20114790 | 12/2001 |
| DE | 10240716 | 3/2004 |

(56) References Cited

FOREIGN PATENT DOCUMENTS

| | | |
|---|---|---|
| DE | 202008004045 | 6/2008 |
| DE | 202008016045 | 4/2009 |
| EP | 0545887 | 6/1993 |
| EP | 1504792 | 2/2005 |
| EP | 1529552 | 5/2005 |
| EP | 1839703 | 10/2007 |
| EP | 1849497 | 10/2007 |
| EP | 1916017 | 4/2008 |
| EP | 2228098 | 9/2010 |
| GB | 2020970 | 11/1979 |
| JP | H05-220231 | 8/1993 |
| JP | 10-295837 | 10/1998 |
| JP | 3075306 B2 | 8/2000 |
| JP | 2008-500846 | 10/2005 |
| JP | 2007267936 A | 10/2007 |
| JP | 2008-73148 | 4/2008 |
| WO | WO9917668 | 4/1999 |
| WO | WO-200002491 | 1/2000 |
| WO | WO-2003047682 | 6/2003 |
| WO | WO2007001364 | 1/2007 |
| WO | WO2007106856 | 9/2007 |
| WO | WO-2007143862 | 12/2007 |
| WO | WO-2008027438 | 3/2008 |
| WO | WO-2010016009 | 2/2010 |
| WO | WO2011097383 | 8/2011 |
| WO | WO2012142427 | 10/2012 |
| WO | WO-2013103743 | 7/2013 |
| WO | WO-2015061773 A1 | 4/2015 |
| WO | WO2015/130891 | 9/2015 |
| WO | WO2016/007798 | 1/2016 |
| WO | WO-2016127120 A1 | 8/2016 |
| WO | WO2016/154343 | 9/2016 |
| WO | WO2016176360 | 11/2016 |
| WO | WO2016203461 | 12/2016 |
| WO | WO2017136891 | 8/2017 |
| WO | WO2018067411 | 4/2018 |
| WO | 2019118773 | 6/2019 |
| WO | WO2019118777 | 6/2019 |

OTHER PUBLICATIONS

Ala-Houhala, MJ., et al., "Comparison of narrow-band ultraviolet B exposures and oral vitamin D substitution on serum 25-hydroxyvitamin D concentration," Br J Dermatol. Apr. 2012. (5 pgs).
Australian Exam Report for co-pending Australian Application No. 2013206887, Applicant: BeneSol, Inc.; Date of Mailing: Feb. 24, 2017, 4 pages.
Bouillon, R., et al., "Action spectrum for production of previtamin D3 in human skin," CIE Technical Report 174, Commission International de l'Eclairage (CIE). 2006. (16 pgs).
Brozyna, et al, "Mechanism of UV-related carcinogenesis and its contribution to nevi/melanoma," Oct. 8, 2008, National Institute of Health Public Access, pp. 2 and 4.
Bruls, WA., et al., "Transmission of UV-radiation through human epidermal layers as a factor influencing the minimal erythema dose," Photochemistry and Photobiology. Jan. 1984. (5 pgs).
Bunker, JWM., et al., "Precise evaluation of ultraviolet therapy in experimental rickets," New England Journal of Medicine. 1937. (6 pgs).
Changaris, DG., et al., "Pulsed UVB Irradiation Converts 7-dehydrocholesterol to previtamin D3 and Photoproducts," 2001. (10 pgs).
Chen, TC., et al., "Factors that influence the cutaneous synthesis and dietary sources of vitamin D," Archives of Biochemistry and Biophysics. Apr. 15, 2007. (4 pgs).
Clemens, TL., et al., "Increased skin pigment reduces the capacity of skin to synthesis vitamin D3," Lancet. Jan. 1982. (3 pgs).
De Fabo, EC., et al., "Mechanism of immune suppression by ultraviolet irradiation in vivo. I. Evidence for the existence of a unique photoreceptor in skin and its role in photoimmunology," The Journal of Experimental Medicine. Jul. 1983. (15 pgs).

Devgun, MS., et al., "Tanning, protection against sunburn and vitamin D formation with a UV-A 'sun-bed'". The British Journal of Dermatology. Sep. 1982. (11 pgs).
Diffey, BL. "Observed and predicted minimal erythema doses: a comparative study," Photochemistry and Photobiology. Oct. 1994. (3 pgs).
Diffey, BL., et al., "A preliminary study on photoaddition and erythema due to UVB radiation," Physics in Medicine and Biology. Apr. 1984. (8 pgs).
English Translation of Japanese Office Action for Application No. 2014-550552, Applicant: BeneSol, Inc.; Date of Mailing: Oct. 4, 2016, 10 pages.
English Translation of Russian Office Action for Application No. 2014131906, Applicant: BeneSol, Inc.; Date of Mailing: Nov. 21, 2016, 10 pages.
English Translation of Second Japanese Office Action for Application No. 2014-550552, Applicant: BeneSol, Inc.; Date of Mailing: Jul. 28, 2017, 8 pages.
Extended European Search Report in Application No. 13733883.6, Applicant: BeneSol, Inc., Date of Mailing: May 12, 2015, 7 pages.
Farr, PM., et al., "The erythemal response of human skin to ultraviolet radiation," The British Journal of Dermatology. Jul. 1985. (13 pgs).
First European Examination Report in Application No. 13733883.6, Applicant: BeneSol, Inc., Date of Mailing: Sep. 1, 2016, 4 pages.
Galkin, ON., et al., "'Vitamin D' viodosimeter: basic characteristics and potential applications," Journal of Photochemistry and Photobiology. Nov. 1999. (8 pgs).
Guilhou, JJ., et al., "Vtiman D metabolism in psoriasis before and after phototherapy," Acta Derm Venereol. 1990. (5 pgs).
Haddad, JG., et al., "Human plasma transport of vitamin D after its endogenous synthesis," J Clin Invest. Jun. 1993. (4 pgs).
Holick, MF. "Environmental factors that influence the cutaneous production of vitamin D," Am J Clin Nutr. Mar. 1995. (8 pgs).
Holick, MF. "Sunlight, UV-radiation, vitamin D and skin cancer: how much sunlight do we need?" Advances in Experimental Medicine and Biology. 2008. (15 pgs).
Holick, MF., et al., "Skin as the site of vitamin D synthesis and target tissue for 1,25-dihydroxyvitamin D3. Use of calcitriol (1,25-dihydroxyvitamin D3) for treatment of psoriasis," Archives of Dermatology. Dec. 1987. (14 pgs).
Holick, MF., et al., "Photosynthesis of previtamin D3 in human skin and the physiologic consequences," Science. Oct. 1980. (3 pgs).
Holick, MF., et al., "Regulation of cutaneous previtamin D3 photosynthesis in man: skin pigment is not an essential regulator," Science. Feb. 1981. (4 pgs).
Holick, MF., et al., "The photoproduction of 1 alpha,25-dihydroxyvitamin D3 in skin: an approach to the therapy of vitamin-D-resistant syndromes," The New England Journal of Medicine. Aug. 1980. (6 pgs).
Hume, EM., et al., "On the Absorption of Vitamin D from the Skin," The Biochemical Journal. 1927. (6 pgs).
International Search Report and Written Opinion for International Application No. PCT/US2014/062352 filed Oct. 27, 2014, Applicant: BeneSol, Inc., Date of Mailing: Feb. 5, 2015, 12 pages.
International Search Report and Written Opinion for International Application No. PCT/US2016/016873 filed Feb. 5, 2016, Applicant: BeneSol, Inc., Date of Mailing: May 5, 2016, 12 pages.
International Search Report and Written Opinion for International Application No. PCT/US2016/029615 filed Apr. 27, 2016, Applicant: BeneSol, Inc., Date of Mailing: Oct. 7, 2016, 14 pages.
Jablonski, NG., et al., "The evolution of human skin coloration," Journal of Human Evolution. Jul. 2000. (50 pgs).
Knudson, A., et al., "Quantitative studies of the effectiveness of ultraviolet radiation of various wave-lengths in rickets," Journal Biological Chemistry. 1938. (13 pgs).
Krause, R., et al., "UV radiation and cancer prevention: what is the evidence?" Anticancer Research. Jul. 2006. (5 pgs).
Lehmann, B., "The vitamin D3 pathway in human skin and its role for regulation of biological processes," Photochemistry and Photobiology. 2005. (6 pgs).
Lehmann, B., et al., "A novel pathway for hormonally active calcitriol," Hormone Research. 2000. (4 pgs).

(56) References Cited

OTHER PUBLICATIONS

Lehmann, B., et al., "Demonstration of UVB-induced synthesis of 1 alpha,25-dihydroxyvitamin D3 (calcitriol) in human skin by microdialysis," *Archives of Dermatological Research*. Apr. 2003. (5 pgs).
Lehmann, B., et al., "Rold for tumor necrosis factor-alpha in UVB-induced conversion of 7-dehydrocholesterol to 1alpha,25-dihydroxyvitamin D3 in cultured keratinocytes," *The Journal of Steroid Biochemistry and Molecular Biology*. May 2004. (5 pgs).
Lehmann, B., et al., "The UVB-induced synthesis of vitamin D3 and 1alpha,25-dihydroxyvitamin D3 (calcitriol) in organotypic cultures of keratinocytes: effectiveness of the narrowband Philips TL-01 lamp (311 nm)." *J Steroid Biochem Mol Biol*. Mar. 2007. (4 pgs).
Lehmann, B., et al., "UVB-induced conversion of 7-dehydrocholesterol to 1 alpha,25-dihydroxyvitamin D3 (calcitriol) in the human keratinocyte line HaCaT," *Photochemistry and Photobiology*. Dec. 2000. (10 pgs).
Lehmann, B., et al., "UVB-induced conversion of 7-dehydrocholesterol to 1alpha,25-dihydroxyvitamin D3 in an in vitro human skin equivalent model," *The Journal of Investigative Dermatology*. Nov. 2001. (7 pgs).
Lesiak, A., et al., "Vitamin D serum level changes in psoriatic patients treated with narrowband ultra violet B phototherapy are related to the season of the irradiation," *Photodermatol Photoimmunol Photomed*. Dec. 2011. (7 pgs).
Liu, W., et al., "Skin phototyping in a Chinese female population: analysis of four hundred and four cases from four major cities of China," *Photodermatology, Photoimmuniology and Photomedicine*. Aug. 2006. (5 pgs).
MacLaughlin, JA., et al., "Spectral character of sunlight modulates photosynthesis of previtamin D3 and its photoisomers in human skin," *Science*. May 1982. (3 pgs).
Marcus, M., "Make Your Day Better With D," *USA Weekend*. Nov. 2011. (3 pgs).
Maughan, G.H. "Ultra-violet wavelengths valuable in the cure of rickets in chickens," *American Journal of Physiology*. 1928. (18 pgs).
McLoone, P., et al., "An action spectrum for the production of cis-urocanic acid in human skin in vivo," *The Journal of Investigative Dermatology*. May 2005. (4 pgs).
Mead, MN. "Benefits of sunlight: a bright spot for human health," *Environmental Health Perspectives*. Apr. 2008. (13 pgs).
Moan, J., et al., "Sunbeds as vitamin D Sources." *Photochemistry and Photobiology*. Nov. 2009. (8 pgs).
Nemanic, MK., et al., "In vitro synthesis of vitamin D-3 by cultured human keratinocytes and fibroblasts: action spectrum and effect of AY-9944," *Biochimica et Biophysica Acta*. Sep. 1985. (11 pgs).
Norval, M. et al., "Is the action spectrum for the UV-induced production of previtamin D3 in human skin correct?" *Photochemical & Photobiological Sciences*. Jan. 2010. (7 pgs).
Obi-Tabot, ET., et al., "A human skin equivalent model that mimics the photoproduction of vitamin D3 in human skin," *In Vitro Cellular & Developmental Biology*. Mar. 2000. (6 pgs).
Olds, WJ., et al., "In vitro model of vitamin D3 (cholecalciferol) synthesis by UV radiation: dose-response relationships," *Journal of Photochemistry and Photobiology*. Nov. 2008. (6 pgs).
Osmancevic, A., et al., "UVB therapy increases 25(OH) vitamin D syntheses in postmenopausal women with psoriasis," *Photodermatol Photoimmunol Photomed*. Oct. 2007. (7 pgs).
Osmancevic, A., et al., "Vitamin D production in psoriasis patients increases less with narrowband thatn with broadband ultraviolet B phototherapy." *Photodermatol Photoimmunol Photomed*. Jun. 2009. (5 pgs).
Osmancevic, A., et al., "Vitamin D status in psoriasis patients during different treatments with phototherapy," *J Photochem Photobiol B*. Nov. 2010. (7 pgs).
Parrish, JA., et al., "Action spectrum for phototherapy of psoriasis," *The Journal of investigative Dermatology*. May 1981. (5 pgs).

Partial Supplementary European Search Report for co-pending European Patent Application No. 14856603.7, Applicant: BeneSol, Inc., Mailed Apr. 13, 2017, 7 pages.
Porojnicu, AC., et al., "Sun beds and cod liver oil as vitamin D sources," *Journal of Photochemistry and Photobiology*. May 2008. (7 pgs).
Ryan, C., et al., "The effect of narrowband UV-B treatment for psoriasis on vitamin D status during wintertime in Ireland," *Arch Dermatol*. Aug. 2010. (8 pgs).
Sage, RJ., et al., "UV-based therapy and vitamin D," *Dermatologic Therapy*. Jan. 2010. (10 pgs).
Scientific Committee on Consumer Products, "Opinion on Biological effects of ultraviolet radiation relevant to health with particular reference to sunbeds for cosmetic purposes," *European Commission Health & Consumer Protection Directorate-General*. 8th plenary of the SCCP on Jun. 20, 2006. (43 pgs).
Stamp, TC., et al., "Comparison of oral 25-hydroxycholecalciferol, vitamin D, and ultraviolet light as determinants of circulating 25-hydroxyvitamin D," *Lancet*. Jun. 25, 1977. (3 pgs).
Suh, KS., et al., "Long-term evaluation of erythema and pigmentation induced by ultraviolet radiations of different wavelengths," *Skin Research and Technology*. May 2007. (8 pgs).
Tangpricha, V., et al., "Tanning is associated with optimal vitamin D status (serum 25-hydroxyvitamn D concentration) and higher bone mineral density." *The American Journal of Clinical Nutrition*. Dec. 2004. (5 pgs).
Terenetskaya, I. "Two methods for direct assessment of the Vitamin D synthetic capacity of sunlight and artificial UV sources," *The Journal of Steroid Biochemistry and Molecular Biology*. May 2004. (4 pgs).
Vahavihu, K., et al. "Heliotherapy improves vitamin D balance and atopic dermatitis," *The British Journal of Dermatology*. Jun. 2008. (6 pgs).
Vantieghem, K., et al., "UVB-induced production of 1,25-dihydroxyvitamin D3 and vitamin D activity in human keratinocytes pretreated with a sterol delta7-reductase inhibitor," *J Cell Biochem*. May 2006. (12 pgs).
Walterscheid, JP., et al., "Cis-urocanic acid, a sunlight-induced immunosuppressive factor, activates immune suppression via the 5-HT2A receptor," *Proc. Natl. Acad. Sci. U.S.A.* Nov. 2006. (6 pgs).
Webb, A.R., et al., "The role of sunlight in the Cutaneous production of vitamin D3," *Annual Review of Nutrition*. 1988. (6 pgs).
Webb, AR., et al., "Sunlight regulates the cutaneous production of vitamin D3 by causing its photodegradation," *The Journal of Clinical Endocrinology and Metabolism*. May 1989. (6 pgs).
Weinstock, MA. "Assessment of sun sensitivity by questionnaire: validity of items and formulation of a prediction rule," *Journal of Clinical Epidemiology*. Aug. 2006. (6 pgs).
Whitmore, SE., et al., "Tanning salon exposure and molecular alterations," *Journal of the American Academy of Dermatology*. May 2001. (6 pgs).
Youn, JI., et al., "Assessment of the usefulness of skin phototype and skin color as the parameter of cutaneous narrow band UVB sensitivity in psoriasis patients," *Photodermatology, Photoimmunology and Photomedicine*. Oct. 2003. (4 pgs).
Extended European Search Report for co-pending European Patent Application No. 17195774.9, Applicant: BeneSol, Inc., Date of Mailing: May 17, 2018, 9 pages.
English translation of Chinese Office Action received for CN Application No. 201610833794.9, Applicant: BeneSol, Inc., Date of Mailing: Aug. 1, 2018, 13 pages.
First Examination Report for co-pending Australian Patent Application No. 2018200369, Applicant: BeneSol, Inc., Date of Mailing: Jun. 22, 2018, 2 pages.
Examiner's Report for co-pending Canadian Patent Application No. 2,861,620, Applicant: BeneSol, Inc., Date of Mailing: Jul. 24, 2018, 4 pages.
Notice of Opposition filed for co-pending European Patent Application No. 13733883.6, issued as 2800605, Applicant: BeneSol, Inc., Date of Mailing: Jul. 31, 2018, 33 pages.
"Ergoline Vitamin D3 Solarium mit Dr. Holick UV-Systems," Sep. 2005, Ergoline GMBH Germany, Internet: www.ergoline. DE, 112 pages.

(56) References Cited

OTHER PUBLICATIONS

"Solaria Köln 2005," International Trade Fair for Sunlight Systems, Oct. 2005, English Google machine translation included, 9 pages.
"Center Wavelength (CW) and Full Width at Half Maximum (GWHM) filter numbers," webpage at http://mdc.custhelp.com/app/answers/detail/a_id/19235/-/center-wavelength-%28cw%29-and-full-width-at-half-maximum-%28fwhm%29-filter-numbers, published Mar. 16, 2011, 1 page.
English Translation of Chinese Office Action for Application No. 201480066635.X, Applicant: BeneSol, Inc., Date of Mailing: Nov. 7, 2017, 11 pages.
Fitzpatrick, "The validity and practicality of sun-reactive skin types I through VI," Arch Dermatol. Jun. 1988, 124(6):869-71, 3 pages.
International Search Report and Written Opinion for International Application No. PCT/US2018/065542 filed Dec. 13, 2018, Applicant: BeneSol, Inc., Date of Mailing: Mar. 26, 2019, 8 pages.
English translation of Chinese Office Action received for CN Application No. 201680021252.X, Applicant: BeneSol, Inc., Date of Mailing: Jan. 18, 2019, 17 pages.
International Search Report and Written Opinion for International Application No. PCT/US2018/065537 filed Dec. 13, 2018, Applicant: BeneSol, Inc., Date of Mailing: Mar. 1, 2019, 10 pages.
Extended European Search Report for European Patent Application No. 16787092.2, Applicant: BeneSol, Inc., Date of Mailing: Jan. 18, 2019, 9 pages.
English translation of Chinese Office Action received for CN Application No. 201680037887.9, Applicant: BeneSol, Inc., Date of Mailing: Mar. 19, 2019, 19 pages.
Extended European Search Report for European Patent Application No. 17858943.8, Applicant: BeneSol, Inc., Date of Mailing: May 12, 2020, 9 pages.
Extended European Search Report received for European Patent Application No. 20183232.6, Applicant: BeneSol, Inc., Date of Mailing: Nov. 24, 2020, 8 pages.
Examiner's Requisition for Canadian Patent Application No. 2,861,620, Date of Mailing Nov. 5, 2021, 3 pages.
Extended European Search Report for European Patent Application No. 18888140.3, Date of Mailing Aug. 25, 2021, 8 pages.
Extended European Search Report for European Patent Application No. 18887658.5, mailing date Sep. 27, 2021, 8 pages.
Extended European Search Report received for European Patent Application No. 21192571.4, Applicant: BeneSol, Inc., Date of Mailing: Feb. 3, 2022, 10 pages.
International Search Report and Written Opinion mailed Feb. 3, 2022 in International Patent Application No. PCT/US21/46578, 17 pages.
International Search Report and Written Opinion mailed Jan. 19, 2018 in International Patent Application No. PCT/US17/54578, 15 pages.
Examiner's Report for Canadian Patent Application No. 2,861,620, Applicant: BeneSol, Inc., Date of Mailing: Jun. 14, 2023, 3 pages.
Extended European Search Report mailed Jul. 23, 2024 for European Patent Application No. 21859096.6, 8 pages.

\* cited by examiner

Please review and confirm

Sep 24 | 12:32 am

You reported no color change after using SOLIUS.

Taking any medications that may make your skin more sensitive to UV light?  Yes ○  No ●

Have you sunbathed or had a tanning or phototherapy treatment in the last 24 hours?  Yes ○  No ●

Exit  Back  Edit  Next

*FIG. 7*

Sep 24 | 12:15 am

If you have no base tan, what is your skin response to 1 hour of noon sunlight in June?

I will have a painful burn at 24 hours and no tan in 7 days

I will have a tender burn at 24 hours and a light tan at 7 days

I will have a slightly tender burn at 24 hours and a moderate tan at 7 days

I will have no burn at 24 hours and a good tan at 7 days

Next

Exit

*FIG. 9*

SYSTEMS AND METHODS FOR OPERATING PHOTOTHERAPY KIOSKS

CROSS REFERENCE TO RELATED APPLICATIONS

This application is a 35 U.S.C. § 371 U.S. National Phase application of International Patent Application No. PCT/US2018/065542, titled "SYSTEMS AND METHODS FOR OPERATING PHOTOTHERAPY KIOSKS," filed Dec. 13, 2018 which claims priority to U.S. Patent Application No. 62/599,242, titled "SYSTEMS AND METHODS FOR OPERATING PHOTOTHERAPY KIOSKS," filed Dec. 15, 2017, U.S. Provisional Patent Application No. 62/599,252, titled "DYNAMIC DOSING SYSTEM FOR PHOTOTHERAPY AND ASSOCIATED DEVICES AND METHODS," filed Dec. 15, 2017, and U.S. Patent Application No. 62/613,745, titled "SYSTEMS AND METHODS FOR OPERATING PHOTOTHERAPY KIOSKS," filed Jan. 4, 2018, the contents of each are hereby incorporated by reference in their entireties.

TECHNICAL FIELD

The present technology is related to the use and control of phototherapeutic systems, devices, and methods, such as phototherapeutic systems well-suited for vitamin D phototherapy and treating skin conditions.

BACKGROUND

Photobiology is the study of light (non-ionizing radiation) interactions with living organisms. Within the field of photobiology is phototherapy, the therapeutic use of light to improve the health of the human body and mind. Since the invention of the electric light bulb, phototherapy has used artificial light to treat diseases such as lupus vulgaris.

Today phototherapy is used in the prevention or treatment of a variety of conditions that impact many systems of the human body. Certain light exposure produces vitamin D as well as several other hormones and peptides that positively impact human health. Modern human indoor lifestyles and fear of the deleterious effects of ultraviolet radiation ("UVR"), such as cancer, prevent many people from receiving adequate sunlight exposure. Thus, phototherapy using artificial light can be beneficial, however, a challenge for UVR based phototherapy applications is delivering an appropriate dose. This is especially true for self-care applications, as the long-term negative effects of UVR are not immediately apparent to the user.

Phototherapy devices have been developed for three major usage environments: medical clinic, at-home, and tanning salons. These are operated based on a user setting a timer for shutting off one or more light bulbs. Most dermatologic devices are designed for a clinical setting, where a technician sets the device timer according to a prescribed treatment regime. Commercial tanning devices are primarily utilized by tanning salons where a technician sets exposure time based on regulatory guidance. At-home versions of tanning devices are used according to the same regulatory guidance. The difference between phototherapy devices used in a medical setting and tanning beds is the spectral output, but the user operation of the two types of devices is essentially the same. Thus, current phototherapy devices are essentially "dumb" lightboxes that require user instruction, regardless of the operational environment, indication of use, prescriptive requirements, user needs, etc.

BRIEF DESCRIPTION OF THE DRAWINGS

FIGS. 7-10 are example user interfaces used in some implementations.

DETAILED DESCRIPTION

The technology presented herein is directed to systems and methods for operating phototherapy system and delivering phototherapy treatment. Various implementations of the phototherapy system can include one or more of: a phototherapy kiosk, a personal computing device, a server system, or any combination thereof. Specific details of several embodiments of the present technology are described herein with reference to FIGS. 1-10. Although many of the embodiments are described with respect to devices, systems, and methods for promoting vitamin D production in skin, other applications and other embodiments in addition to those described herein are within the scope of the present technology. For example, at least some embodiments of the present technology may be useful for providing phototherapeutic treatment for skin diseases. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

Figure 1A:
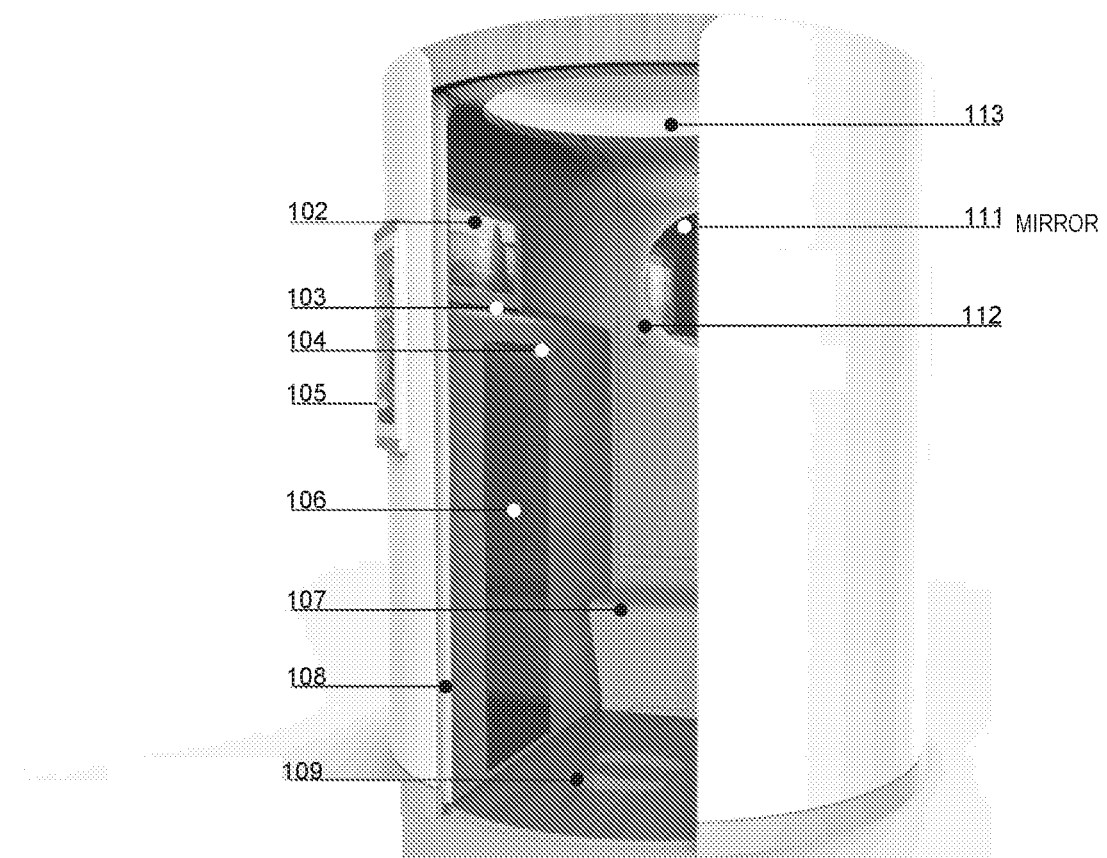
FIG. 1A is an illustration of an example phototherapy kiosk used in some implementations.

As shown in FIG. 1A, a phototherapy kiosk is a device with a radiation emission component for delivering UVR based photo therapy. The phototherapy kiosk includes a phototherapeutic assembly 106, such as a panel including one or more UV radiation assemblies configured to emit UV radiation within a predetermined spectrum. Suitable UV radiation assemblies and configurations are disclosed in U.S. patent application Ser. No. 13/733,860, titled "PHOTOTHERAPEUTIC APPARATUS FOR FOCUSED UVB RADIATION AND VITAMIN D SYNTHESIS AND ASSOCIATED SYSTEMS AND METHODS" and U.S.

Provisional Patent Application No. 62/403,590, titled "PHOTOTHERAPEUTIC SYSTEMS INCLUDING SPREADING AND COLLIMATING FEATURES AND RELATED TECHNOLOGY," both of which incorporated herein by reference in their entireties. The phototherapy kiosk can be a booth that is completely or partially enclosed with a lockable or non-lockable door 108 (e.g., a pocket door) so that users have a private and secure environment to disrobe for treatment. The phototherapy kiosk design reduces or minimizes skin to device contact for improved sanitation. In some implementations, the phototherapy kiosk can be a laydown style device similar to a traditional tanning bed. Protective eyewear is frequently used in UVR based phototherapy to prevent eye damage from optical radiation and the phototherapy kiosk can have an integrated eyewear dispenser 103 that is operated by a user interface. In some implementations, the phototherapy kiosk can have a LED lighting 110 that can be adjusted (color, lighting level, patterns, changing effects, etc.) based on stages of use, communication emphasis, entertainment or user interaction. In some implementations, the phototherapy kiosk can have one or more user interface components 102 (e.g. with device operation instructions) and 105 (e.g. with kiosk information such as a waitlist, as described below. In various implementations, the phototherapy kiosk can have one or more of: an emergency stop control 104, a bench 107, positioning indicators 109 (e.g., footprints), a mirror 111, or a coat hook 112, overhead, power outage, or mood lighting 113. One or more of devices (e.g., the phototherapy kiosk of FIG. 1A) associated with a phototherapy system, or interactions between these devices, can provide phototherapy system functions such as: user account management, skin type evaluation, treatment parameter determinations and adjustments, treatment blocking or warnings for some hazard prevention, treatment session purchases, treatment education and guidance, session records access, treatment regime determination, facility access and session scheduling, converting treatment parameter determinations into kiosk controls, and environment and entertainment settings for treatment sessions. Additional details on the phototherapy system functions are provided below in relation to FIGS. 3, 5, and 6.

The phototherapy system functions can be performed based on user input, records of user data, guidelines and algorithms for treatment parameter selection, direct measurements, etc. These data sources can be access or implemented though one or more of: a phototherapy kiosk, a personal computing device, a server system, a third-party system, or any combination thereof. For example, these data sources can be a local or networked database, input through a web services platform, input on mobile device app, input through a web browser, input through a connected touchscreen or other input device, sensors, etc. In various implementations, some of the phototherapy system functions are accomplished through a combination of inputs from a phototherapy kiosk, a personal computing device, a server system, or any combination thereof. For example, a user can establish a user profile though interactions with either or both of the phototherapy kiosk or a mobile device. The mobile device can communicate user information for the user profile directly to a phototherapy kiosk or through a server system in communication with a phototherapy kiosk. Additional details regarding various communications paths and interactions between devices are provided below in relation to FIGS. 4 and 5.

In various implementations, one or more of these phototherapy system functions can be facilitated though an interactive user interface. An interactive user interface can deliver dynamic audio/video, questions, instructions, status indicators, etc. and can obtain user input. An interactive user interface can be provided through one or more display devices integrated with a phototherapy kiosk or through a personal computing device such as a mobile phone, tablet, wearable device, personal computer, etc. For example, a phototherapy kiosk can have a monitor attached on the inside and another attached on the outside (See e.g. FIG. 1A). Each monitor can display different information and receive input from different users at the same time. However, in other embodiments user interaction with a phototherapy kiosk can be made with only one monitor on the inside or outside of the device. In some embodiments, a user interface can be provided through a portable touchscreen, e.g. using a smartphone application that has a data path to the phototherapy kiosk. In some implementations, a user interface can have audio capability (i.e. speaker) that can be used to deliver music, verbal instructions, or relevant information that augments or is duplicative of visual content. In some implementations, the user interface can incorporate a microphone with voice recognition software that can be used by the user to execute device operational commands as well as provide responses to questions. Some example user interfaces are provided in relation to FIGS. 7-10.

Figure 1B:
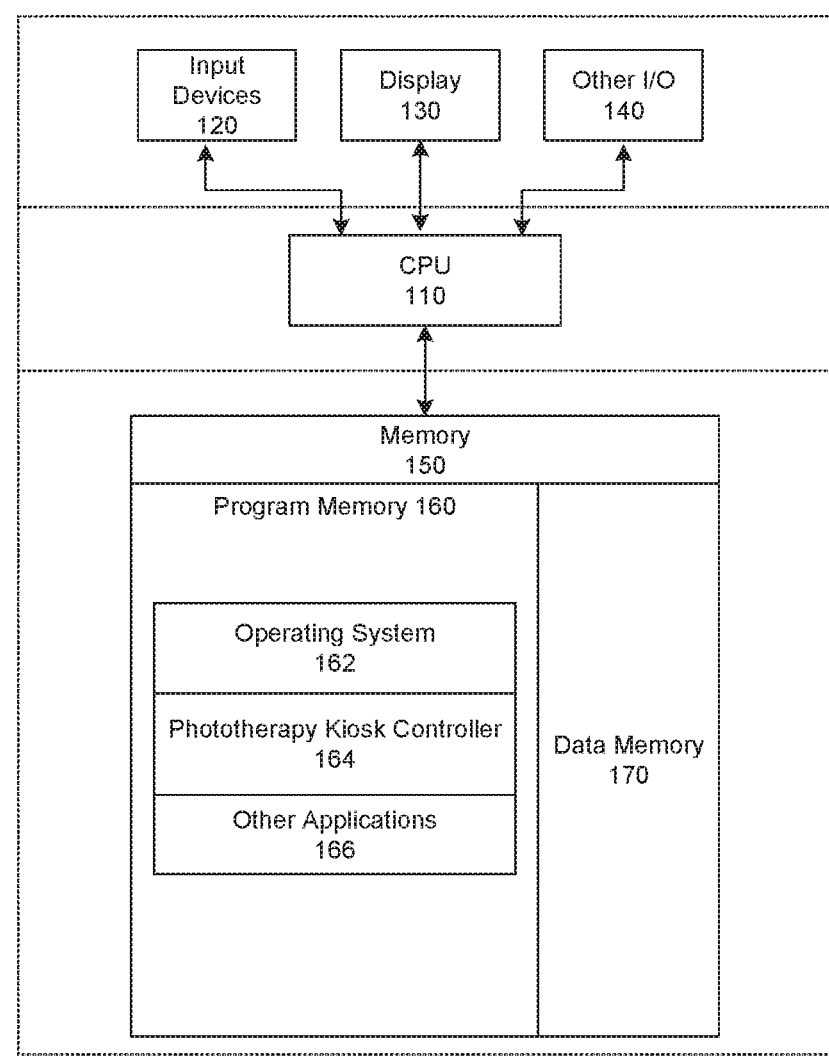
FIG. 1B is a block diagram illustrating an overview of devices on which some implementations can operate.

FIG. 1B is a block diagram illustrating an overview of devices on which some implementations of the disclosed technology can operate. The devices can comprise hardware components of a device 100 that can control a phototherapy kiosk. In some implementations, device 100 can be integrated into the phototherapy kiosk, can be a server system in communication with the phototherapy kiosk, or can be a personal computing device either directly in communication with the phototherapy kiosk or in communication with the server system. Device 100 can include one or more input devices 120 that provide input to the CPU(s) (processor) 110, notifying it of actions. The actions can be mediated by a hardware controller that interprets the signals received from the input device and communicates the information to the CPU 110 using a communication protocol. Input devices 120 include, for example, a touchscreen, a touchpad, a microphone, a wearable input device, a camera or image-based input device, a mouse, a keyboard, a temperature sensor, a motion sensor, a pressure pad, ultrasound sensor, a contact switch, a current sensor, an iridescence sensor, or other user input devices.

CPU 110 can be a single processing unit or multiple processing units in a device or distributed across multiple devices. CPU 110 can be coupled to other hardware devices, for example, with the use of a bus, such as a PCI bus or SCSI bus. The CPU 110 can communicate with a hardware controller for devices, such as for a display 130. Display 130 can be used to display text and graphics. In some implementations, display 130 provides graphical and textual visual feedback to a user. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 140 can also be coupled to the processor, such as a network card, video card, audio card, USB, firewire or other external device, camera, printer, speakers, storage drive, etc. In some implementations, the device 100 also includes a communication device capable of communicating wirelessly or wire-based with a network node. The communication device can communicate with another device or a server through a network using, for example, TCP/IP protocols. Device 100 can utilize the communication device to distribute operations across multiple network devices.

The CPU 110 can have access to a memory 150 that is in device 100 or distributed across multiple devices. A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 150 can include program memory 160 that stores programs and software, such as an operating system 162, phototherapy kiosk controller 164, and other application programs 166. Memory 150 can also include data memory 170 that can include user profile information, treatment parameters, kiosk usage history, user question responses, medical data, configuration data, settings, user options or preferences, etc., which can be provided to the program memory 160 or any element of the device 100.

Some implementations can be operational with numerous other computing system environments or configurations. Examples of computing systems, environments, and/or configurations that may be suitable for use with the technology include, but are not limited to, phototherapy kiosks, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
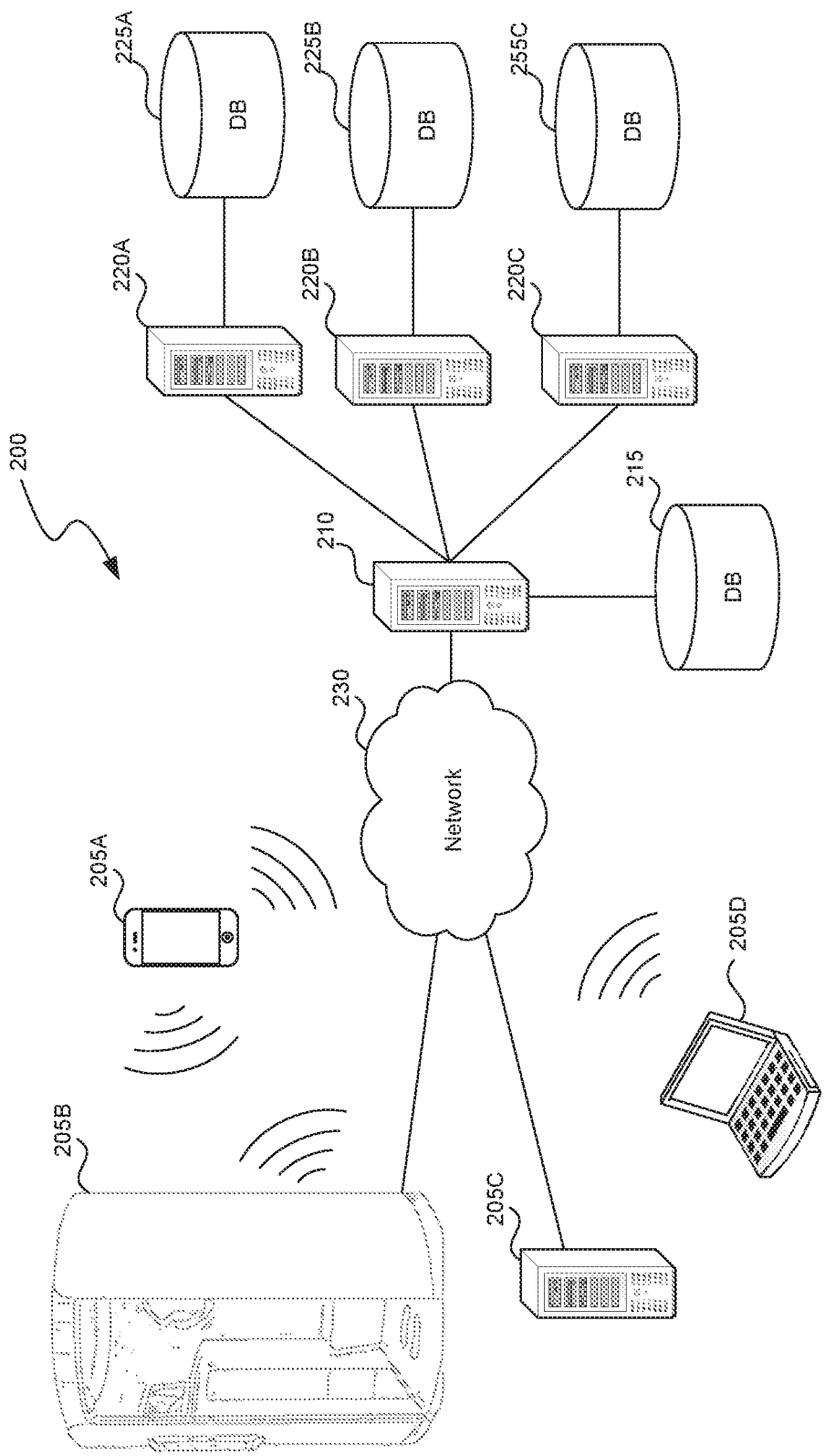
FIG. 2 is a block diagram illustrating an overview of an environment in which some implementations can operate.

FIG. 2 is a block diagram illustrating an overview of an environment 200 in which some implementations of the disclosed technology can operate. Environment 200 can include one or more client computing devices 205A-D, examples of which can include device 100. For example, Device 205A is a mobile computing device, device 205B is a phototherapy kiosk, device 205C is a server system, and device 205D is a personal computer. Client computing devices 205 can operate in a networked environment using logical connections 210 through network 230 to one or more remote computers, such as a server computing device.

In some implementations, server 210 can be an edge server which receives client requests and coordinates fulfillment of those requests through other servers, such as servers 220A-C. Server computing devices 210 and 220 can comprise computing systems, such as device 100. Though each server computing device 210 and 220 is displayed logically as a single server, server computing devices can each be a distributed computing environment encompassing multiple computing devices located at the same or at geographically disparate physical locations. In some implementations, each server 220 corresponds to a group of servers.

Client computing devices 205 and server computing devices 210 and 220 can each act as a server or client to other server/client devices. Server 210 can connect to a database 215. Servers 220A-C can each connect to a corresponding database 225A-C. As discussed above, each server 220 can correspond to a group of servers, and each of these servers can share a database or can have their own database.

Databases 215 and 225 can warehouse (e.g. store) information such as user account data, session history, treatment parameter selection criteria, medical records, etc. Though databases 215 and 225 are displayed logically as single units, databases 215 and 225 can each be a distributed computing environment encompassing multiple computing devices, can be located within their corresponding server, or can be located at the same or at geographically disparate physical locations.

Network 230 can be a local area network (LAN) or a wide area network (WAN), but can also be other wired or wireless networks. Network 230 may be the Internet or some other public or private network. Client computing devices 205 can be connected to network 230 through a network interface, such as by wired or wireless communication. While the connections between server 210 and servers 220 are shown as separate connections, these connections can be any kind of local, wide area, wired, or wireless network, including network 230 or a separate public or private network.

Figure 3:
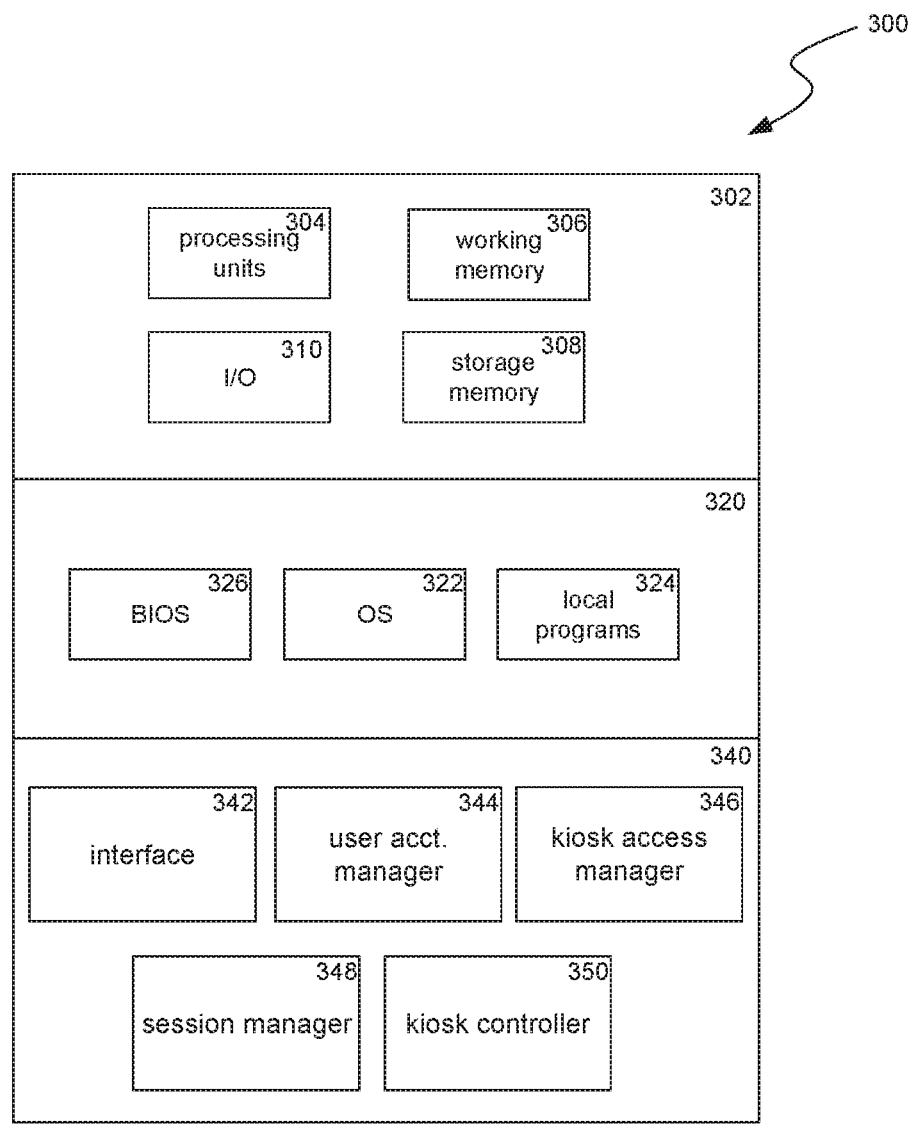
FIG. 3 is a block diagram illustrating components which, in some implementations, can be used in a system employing the disclosed technology.

FIG. 3 is a block diagram illustrating components 300 which, in some implementations, can be used in a system employing the disclosed technology. The components 300 include hardware 302, general software 320, and specialized components 340. As discussed above, a system implementing the disclosed technology can use various hardware including processing units 304 (e.g. CPUs, GPUs, APUs, etc.), working memory 306, storage memory 308 (local storage or as an interface to remote storage, such as storage 215 or 225), and input and output devices 310. In various implementations, storage memory 308 can be one or more of: local devices, interfaces to remote storage devices, or combinations thereof. For example, storage memory 308 can be a set of one or more hard drives (e.g. a redundant array of independent disks (RAID)) accessible through a system bus or can be a cloud storage provider or other network storage accessible via one or more communications networks (e.g. a network accessible storage (NAS) device, such as storage 215 or storage provided through another server 220). Components 300 can be implemented in a client computing device such as client computing devices 205 or on a server computing device, such as server computing device 210 or 220.

General software 320 can include various applications including an operating system 322, local programs 324, and a basic input output system (BIOS) 326. Specialized components 340 can be subcomponents of a general software application 320, such as local programs 324. Specialized components 340 can include user account manager 344, kiosk access manager 346, session manager 348, kiosk controller 350, and components which can be used for providing user interfaces, transferring data, and controlling the specialized components, such as interface 342. In some implementations, components 300 can be in a computing system that is distributed across multiple computing devices or can be an interface to a server-based application executing one or more of specialized components 340.

User account manager 344 can create, update, and delete user accounts. User account manager 344 can be implemented or accessed through a user's personal computing device, a user interface at a phototherapy kiosk, or through a web interface to a server system. User account manager 344 can provide forms and questions to a user to identify user information such as skin type, gender, age, etc. User account manager 344 can also store user session logs, such as the treatment parameters used and treatment results.

Additional details regarding the functions of user account manager 344 are provided below in relation to blocks 504-508 and 542 of FIG. 5.

Kiosk access manager 346 can provide user services to locate and access a phototherapy kiosk. Kiosk access manager 346 can provide a user interface at a user's personal computing device, at a phototherapy kiosk, or through a web interface to a server system. The user interface provided by kiosk access manager 346 can provide a map or listing of phototherapy kiosks, which can be filtered or sorted and can provide corresponding details such as facility or phototherapy kiosk availability times. The user interface provided by kiosk access manager 346 can also provide functions for a user to schedule a session on a particular phototherapy kiosk or to be added to the phototherapy kiosk's waitlist. Additional details regarding the functions of kiosk access manager 346 are provided below in relation to blocks 516-522 of FIG. 5.

Session manager 348 can obtain data sources comprising one or more of: user account information, a remote payload, user input, phototherapy kiosk measurements, or any combination thereof; determine treatment parameters based on the data sources; transform the treatment parameters into kiosk controls; and use kiosk controller 350 to operate the phototherapy kiosk using the kiosk controls. Additional details regarding the functions of session manager 348 are provided below in relation to blocks 526-542 of FIG. 5 and in relation to FIG. 6.

Kiosk controller 350 can include a mapping of treatment parameters to device actuations of the phototherapy kiosk. Treatment parameters specify treatment specifics such as radiation duration, intensity, wavelength filters, and skin areas to treat. Kiosk controls are the instructions to the specific devices embodied in the phototherapy kiosk that implement these parameters. For example, a treatment parameter specifying treatment duration can be converted into a timer setting on one or more radiation lamps. The kiosk controls generated for a set of treatment parameters (and for other session parameters such as environment settings) can then be used to effect actions of the phototherapy kiosk. Additional details regarding the functions of kiosk controller 350 are provided below in relation to block 534-536 of FIG. 5 and block 614 of FIG. 6.

Figure 4:
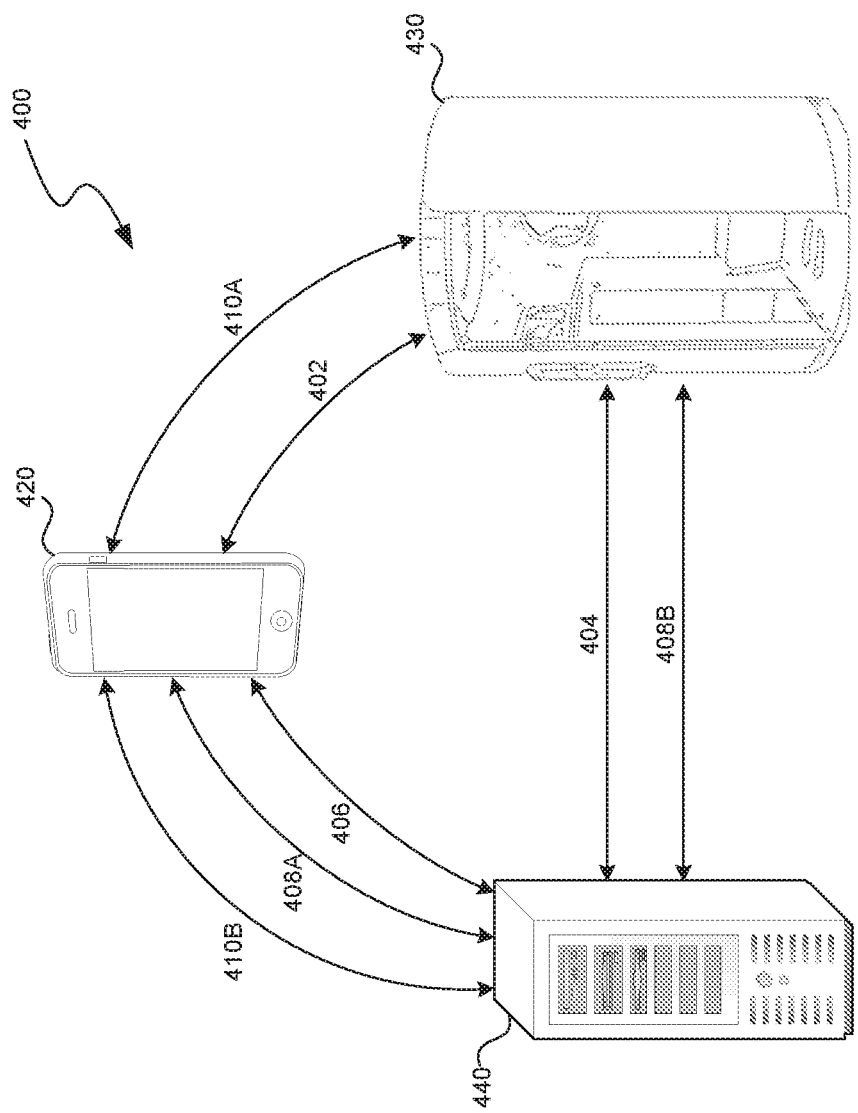
FIG. 4 is a partially schematic view of a phototherapy system illustrating various communication paths that the phototherapy system can implement in accordance with embodiments of the disclosed technology.

FIG. 4 is a block diagram illustrating various communication paths 400 that the phototherapy system can utilize. Communication paths 400 can implement various communication types such as WiFi, Near Field Communication (NFC), Bluetooth, a wired connection such as Ethernet or USB, optical code reading such as the display and reading of a QR Code, etc. In addition to a phototherapy kiosk 430, in various implementations, the phototherapy system can incorporate or operate in conjunction with one or both of a personal computing device 420 or a server system 440. Personal computing device 420 can include, for example, a cell phone, tablet, or personal computer. A server system 440 can be a central system that provides service to users through their personal computing devices and coordinates actions such as scheduling sessions, gathering results, determining treatment parameters, and interfacing with third-party providers. Through these devices, data sources can be accesses including: local or networked databases, input from a web services platform, mobile device input, web browser input, and phototherapy kiosk input. The content of the data obtained and how it is transformed into kiosk controls are described below in relation to FIGS. 5 and 6.

The phototherapy system can utilize a communication path 402 between personal computing device 420 and phototherapy kiosk 430. The phototherapy system can utilize communication path 402 to provide information to phototherapy kiosk 430 from personal computing device 420. For example, a user can create a user profile, answer skin type, age, gender and other biographic questions, select treatment preferences, select phototherapy kiosk environment settings, etc. through the personal computing device 420. These can be transferred to the phototherapy kiosk or can be converted by the personal computing device 420 to phototherapy kiosk controls, at the personal computing device 420, which can be transferred to the phototherapy kiosk 430. The phototherapy system can also utilize communication path 402 to provide feedback from phototherapy kiosk 430, for display by personal computing device 420, about the status of the phototherapy kiosk or current treatment session. For example, a user interface implemented on personal computing device 420 can display a waitlist for the phototherapy kiosk, current session treatment parameters (e.g. time remaining), environment levels and controls for the phototherapy kiosk (e.g. lighting, temperature), etc.

The phototherapy system can utilize communication path 404 between phototherapy kiosk 430 and server system 440. Server system 440 can store user information such as biographics, session history, treatment plans, etc. This data can be provided, via communications path 404, to phototherapy kiosk 430. In some implementations, server system 440 can implement algorithms, such as process 600, to generate kiosk controls, which can be provided to the phototherapy kiosk 430 using communications path 404. Phototherapy kiosk 430 can also provide status and session result data, such as user answers to post-session questions, to server system 440 via communications path 404.

The phototherapy system can utilize communication path 406 between personal computing device 420 and server system 440 to facilitate operations of a phototherapy app executing on personal computing device 420. For example, server system 440 can provide information about phototherapy kiosk facility locations, phototherapy kiosk availability, etc. User interactions through the personal computing device 420 can also provide user profile data such as answers for skin type, age, gender and other biographic questions, treatment preferences, phototherapy kiosk environment settings, etc. In some implementations, this information can be provided to server system 440 through communications path 406, where server system 440 manages the user profile information, e.g. by providing analytics, determining treatment parameters, managing session purchases, etc.

In some implementations, instead of using a direct communications path 402, the phototherapy system can utilize communication path 408 (comprising paths 408A and 408B) between personal computing device 420 and phototherapy kiosk 430, via server system 440. For example, phototherapy kiosk 430 may have no means of direct communication with personal computing device 420, yet personal computing device 420 and phototherapy kiosk 430 can implement the same functions described above in relation to communications path 402, using server system 440 as an intermediary.

In some implementations, instead of using a direct communications path 404, the phototherapy system can utilize communication path 410 (comprising paths 410A and 410B) between phototherapy kiosk 430 and server system 440, via personal computing device 420. For example, phototherapy kiosk 430 may have no wide area communications capabilities, yet phototherapy kiosk 430 and server system 440 can implement the same functions described above in relation to communications path 404, using personal computing device 420 as an intermediary.

Those skilled in the art will appreciate that the components illustrated in FIGS. 1-4 described above, and in each of the flow diagrams discussed below, may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Figure 5:
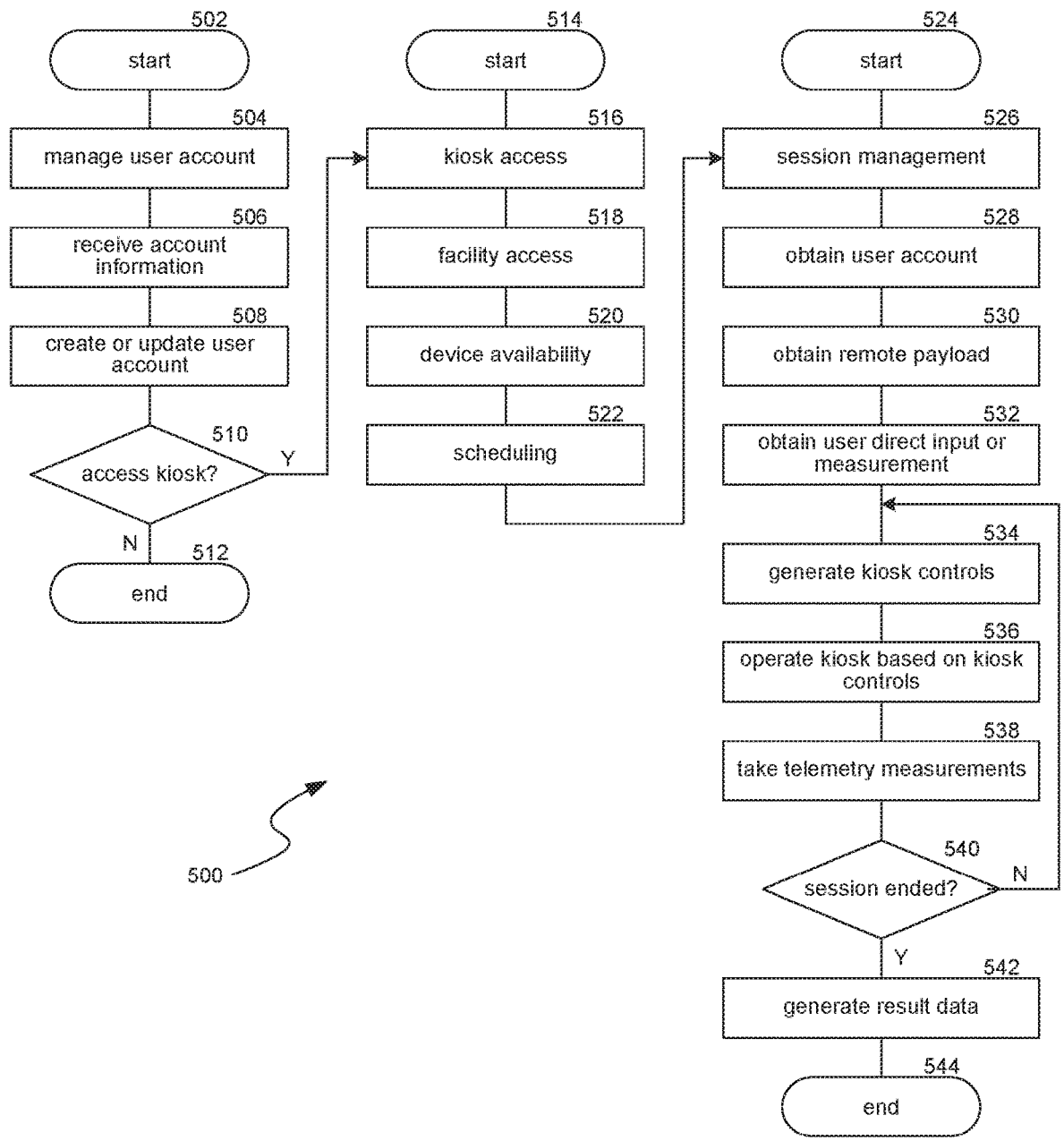
FIG. 5 is a flow diagram illustrating a process used in some implementations for managing kiosk operations and related systems.

FIG. 5 is a flow diagram illustrating a process 500 used in some implementations for managing kiosk operations and related systems. As discussed above, the phototherapy system can be implemented with multiple configurations such as with a standalone phototherapy kiosk or a phototherapy kiosk in conjunction with one or both of a personal computing device or a server system. In addition, various functions of the phototherapy system can be equally implemented through various of the devices which make up the phototherapy system. For example, a user may be able to answer skin-typing questions and enter other biometrics when establishing a user profile through their mobile device, through interaction with a web interface to a server system, or using a user input device coupled to the phototherapy kiosk. As another example, kiosk access functionality, such as scheduling options or waitlist functionality, can be available through the mobile device, web interface, or phototherapy kiosk user interfaces. As a further example, session management such as obtaining data related to treatment, converting these into treatment parameters, using the treatment parameters and obtained session environment settings to generate kiosk controls can be performed locally at the phototherapy kiosk, at a mobile device, or at a server system. Furthermore, depending on a user's goals, process 500 for managing kiosk operations and related systems can begin at one of blocks 502 for managing a user account, 514 for kiosk access functionality, or 524 for session management.

In some implementations, process 500 begins at block 502 and continues to block 504 where a user makes a selection for managing a user account. This can be a selection made at a phototherapy kiosk, through a web interface to a server system, or using a mobile device application. The selection can be a login procedure to an existing user account, and "update profile" selection for an existing user account, or a selection to create a new user account. A user profile can be used as part of a process for: making a payment, getting a treatment session, scheduling a treatment session, obtaining access to a phototherapy kiosk, accessing user records, assessing treatment quality, fraud prevention, user communication (e.g. sales, medical, news), or vandalism prevention.

At block 506, process 500 can receive user account information. User account information can include, for example, birthdate, ID validation information (e.g. DMV, credit agency, or security certificate), user preferences, avatar and alias selection and customization, skin type question responses, treatment regime information, treatment session reminders, medical records, links to external accounts (e.g. Google Fit or Apple health), billing information, account access control or authorization information, session history, session environment settings, logs of previous session results, etc. For example, during a registration process, a Medication List user interface can present questions asking if the user is on any medication that makes their skin photosensitive (more likely to sunburn) and provides a list of medicines that may have this effect. Users can indicate medications, press "Y" or "N" buttons, or provide other "yes" or "no" commands in answer. Users medications can be stored as part of their user profile, which in turn can be used for determining treatment parameters or in a usability check prior to initiating a treatment session.

At block 508, process 500 can create or update a user account using the information received at block 506. The user account can be stored at a server system, on a user's personal computing system, or by one or more phototherapy kiosks.

At block 510, process 500 continues to block 516 if the user indicates they would like to set up a treatment session with a phototherapy kiosk. For example, if process 500 is being performed where user input is received through an input component integrated with a phototherapy kiosk, process 500 can continue to block 516 to set up a session with that phototherapy kiosk. As another example, if process 500 is being performed where user input is received through a mobile device, and after managing their user account, the user makes a selection to access the kiosk (e.g. using a "find a facility" function or a "schedule session" function), process 500 can continue to block 516. Alternatively, if the user does not indicate they want to access a kiosk, process 500 can continue from block 510 to block 512, where it ends.

In some implementations, process 500 begins at block 514 and continues to block 516. For example, a user may select a "find a facility" function or a "schedule session" function through a mobile device app or website interface to a server system. As another example, process 500 may begin at block 514 if a user accesses a schedule feature through a user interface provided by a phototherapy kiosk.

At block 516, process 500 can provide a user interface for kiosk access functionality, such as locating a facility that has a phototherapy kiosk, determining availability of individual phototherapy kiosks, scheduling a phototherapy kiosk treatment session, or adding to a phototherapy kiosk waitlist. While process 500 is shown in sequential order from blocks 518-522, depending on user selections and settings, the order of these blocks can be rearranged or blocks can be omitted.

At block 518, process 500 can provide functionality for accessing a facility with a phototherapy kiosk, such as providing a list or map of facilities and corresponding information. In some implementations, this list or map can have various filtering or sorting capabilities based on one or more of: facility address, proximity to a current user, travel time, postal code, facility hours, device availability, facility type, facility membership requirements, available treatment type(s), loyalty tier, facility rating, or any combination thereof.

At block 520, process 500 can provide device availability options to a user. For example, device availability can be provided for phototherapy kiosks at one or more facilities selected from the list or map provided at block 518. Device availability can be based on facility operation hours, phototherapy kiosk operation hours, wait list counts, average wait duration, etc. Availability options can also indicate a user's position on a waitlist (discussed below).

In some implementations a phototherapy kiosk can have one of three states: "available": meaning ready to use; "ready for": meaning the kiosk is waiting for a particular user to start their scheduled treatment; or "in use": meaning someone is currently using the phototherapy kiosk. In some implementations, when the phototherapy kiosk is in one of the "ready for" or "in use" states, the current user's first and last name initials (or other icon, picture, avatar, identifying character, etc.) can be displayed. When the device is not available an estimated wait time can be provided to indicate the approximate number of minutes a person would need to wait for the next available treatment. If additional people are waiting to use the device after the current user, the estimated start time of each person's treatment can display next to their initials or other icon in a "Waitlist."

At block 522, process 500 can enable a user to schedule a session with a phototherapy kiosk. Scheduling a session can include reserving a block of time or adding a user to a waitlist. In some implementations, the scheduling system can use geo-fencing, e.g. to prevent scheduling or check-in if a user is outside range or alert a user to check-in when the user is within range. In some implementations, process 500 can prevent scheduling to particular phototherapy kiosks for various reasons such as: if that phototherapy kiosk has an identified malfunction, if the phototherapy kiosk has a long wait time, if the user is attempting to schedule a session outside of facility hours for the phototherapy kiosk, if the user's treatment history indicates there may be health concern with scheduling a session, if the user has not had enough time since their last session, or based on a membership type assigned to the user. In some implementations user scheduling can be prioritized based on a number of factors, such as using a FIFO algorithm, user proximity, previous user treatment data, time since last treatment, loyalty tier, if the user did not start treatment within allocated time, if the user cancelled treatment, or system availability.

Figure 8:
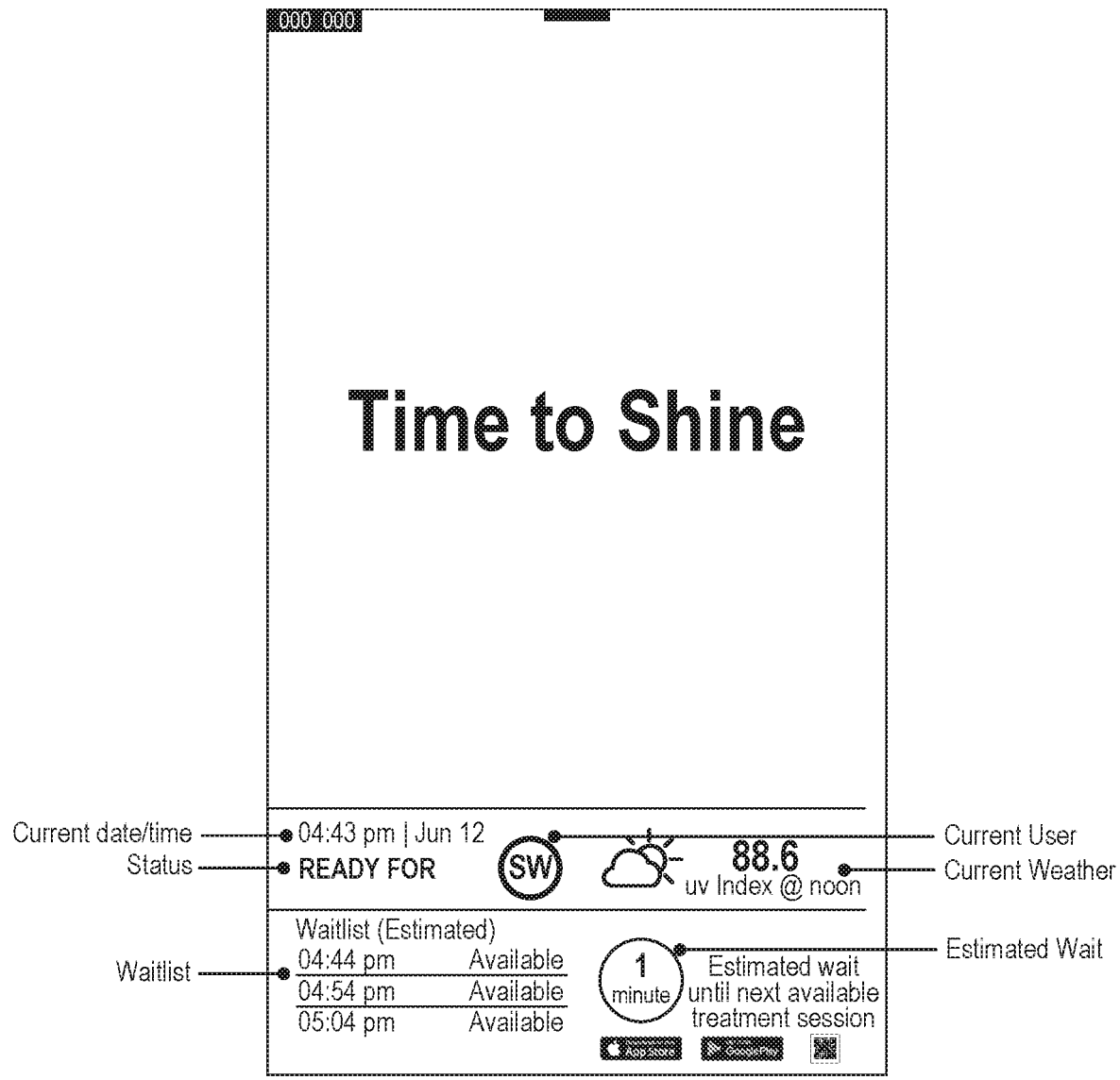
Figure 10:
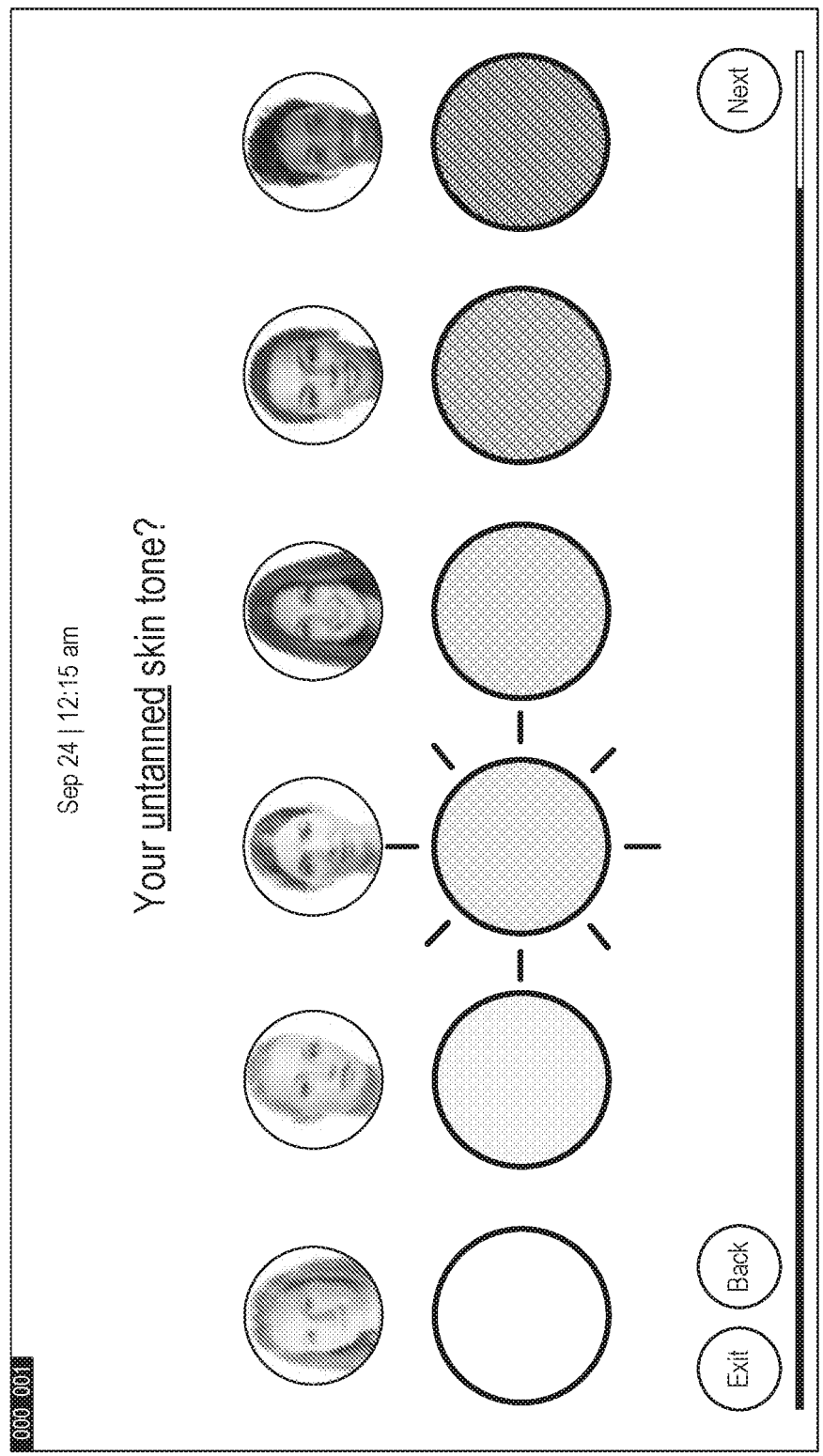

In some implementations, a user can be added to a waitlist and a user interface (e.g. on a mobile device or on the phototherapy kiosk) can be a waitlist monitor containing information about device availability (FIG. 8). A user can add themselves to a phototherapy kiosk waitlist using a smartphone application, by touching an "add to waitlist" button on an integrated phototherapy kiosk waitlist monitor, or by texting a code to a number. In various implementations, from this user interface, users can see the device status, current user, position on the waitlist, or estimated wait time. Users can be removed from the waitlist when the device is in a "ready for" state and their identifying icon is displayed as the next user. The waitlist can display current weather conditions and the UV index to inform users of potential sunburn conditions related to additional outdoor sun exposure. The waitlist display can also include general information such as the current date and time. The waitlist screen can be used to display photographic or video information about the phototherapy kiosk, instructions for use, educational videos, advertisements, or entertainment videos.

At block 526, process 500 can initiate treatment session management for a particular session. In various implementations, process 500 can arrive at block 526 for treatment session management by beginning at block 524 and continuing to block 526; by continuing to block 526 as an alternative to going to block 516 from block 510; or by proceeding from block 522 after a treatment session has been scheduled, and the user is at the phototherapy kiosk to begin a session. In some implementations, at block 526, process 500 can initiate session management in response to a user entering the phototherapy kiosk, identified based on a user interaction with the phototherapy kiosk, a state of the phototherapy kiosk's door, a sensor identifying motion or pressure within the phototherapy kiosk, or communication with the user's mobile device.

At block 528, process 500 can obtain user account information. In some implementations, the user account information can be entered through a user interface integrated with the phototherapy kiosk. In some implementations, the user account information can be obtained through communications with an external device, such as the user's mobile device or a server system. For example, the user account information can be obtained from where it was stored at block 508.

At block 530, process 500 can obtain a remote payload from a system external to the phototherapy kiosk. A payload can include any type of data relevant to treatment parameter settings or phototherapy kiosk environment settings, such as skin type, dose instructions, recent sun/UV exposure, contraindications, SPF usage within previous 24 hours, treatment history, user preferences, etc. In some implementations, the remote payload can be obtained from a linked external database, e.g. via an API, such as Apple Health, a database for a dermatology practice, or a healthcare network. In some implementations, the link to an external database can be established based on a prescription or token from a dermatologist. For example, a dermatologist can specify a treatment regimen and provide a user with a corresponding code. Upon the user entering the code, that phototherapy kiosk can retrieve the treatment regimen. In some implementations, payload can be obtained through interactions with the user's mobile device. For example, the user can specify general session preferences or set up parameters for a particular session when scheduling the session through their mobile device. The mobile device can transfer the information to the phototherapy kiosk or can convert information into kiosk controls, which it transfers to the phototherapy kiosk to be available when the user arrives at the phototherapy kiosk. The mobile device payload can be transferred to the phototherapy kiosk, e.g. using Bluetooth, near field communication, Wi-Fi, a wired connection, through communication with a central server, or another communications channel. In some implementations, the payload can be delivered to the phototherapy kiosk through a visual encoding, such as a barcode or QR code. For example, a mobile device can encode data in a QR code which is displayed on the mobile device's screen, which can be scanned when the user arrives at the phototherapy kiosk. In some implementations, when a user schedules a session through a system other than the phototherapy kiosk directly, the user can receive a code or barcode. When the user enters the code at the phototherapy kiosk, the phototherapy kiosk can obtain information about the session from a central server system.

At block 532, process 500 can obtain user direct input to the phototherapy kiosk or measurements related to the user at the phototherapy kiosk. For example, a series of predetermined questions can be asked of the user, spectrophotometer or colorimeter measurements can be taken, photo or infrared images can be captured, etc. In some implementations, the pre-treatment questions can be answered during the scheduling process and the answers given during that process can be presented to the user for verification. If users need to edit any answer, they can use an "Edit" command to answer the pre-treatment questions again (FIG. 7).

Any device that uses UVR can cause sunburn. To reduce risk, the phototherapy system can obtain skin typing information, e.g. through user questions or other method such as a reflectance spectrophotometer or colorimeter to determine melanin content or concentration prior to treatment. Skin typing facilitates determining treatment parameters that will be efficacious. Depending on when and how the user entered this information, process 500 can obtain this information at any of blocks 528-532. In some implementations, a user can be asked to self-select from among a set of pictures that contain associated skin type characteristics—such as hair color, eye color, skin tone, freckles, facial features, ethnic heritage, or sunburn tendency. Reference pictures can be displayed on a calibrated color-accurate output, such a monitor display or printed medium.

For example, a Skin Tone page (FIG. 10) can be used to select a skin type classification by asking users to self-assess untanned skin tone to estimate melanin content. The Skin Tone page can ask for one of six multiple choice answers to be selected before proceeding. Skin tone swatches and/or pictures of quintessential skin type examples can be presented to the user to assist in selection. In some embodiments, written or audio descriptions of skin tones can be used, such as "pinkish white, pale white, moderate white, medium, dark, or very dark." In some embodiments, questions can be "How easily do you sunburn without a base tan," "How easily can you suntan," "What is your natural eye color," "What is your natural hair color." These questions can be asked in addition or instead of the Sun Response page (FIG. 9) and Skin Tone page (FIG. 10) questions or in various combinations.

A Sun Response page (FIG. 9) can be used to determine the users individual sun sensitivity and preliminary treatment parameters. This page can present questions about the user's skin reaction to sun exposure and can ask for one of four multiple choice answers to be selected before proceeding. This is the classic Fitzpatrick Skin Type self-assessment test and can be used alone to determine skin types I to IV. However, these questions can be combined with other questions to increase accuracy or further classify skin types V and VI which may not be classified in an original self-evaluation test.

Skin typing information can also be obtained from other sources such as measurements taken or questions presented when a user completed a previous session. For example, the system can measure spectral irradiance at the treatment location or ask a user to provide a descriptor for results of their completed session. Alternatively or in addition a payload from a dermatologist can include skin typing information. Furthermore, skin typing information can be based on spectrophotometer or colorimeter measurement device. Such measurements can be input directly from a measurement device into the system or read by the user and manually inputted into the system (e.g. where the measurement device is remote from the phototherapy kiosk).

Also at block 532, user input can be obtained to select a condition to be treated or a therapy type. For example, a treatment selection page can contain a list of medical indications or treatment options for selection. When the user selects an indication, the system can adjust treatment parameters (see process 600 described below). A user can also customize session environment controls such as sound, language, messaging, entertainment, light, or temperature, e.g. through direct user input to the phototherapy kiosk, preferences specified in a user profile, or configurations to a session scheduling.

At block 534, process 500 can generate kiosk controls based on the information obtained in blocks 528-532. In some implementations, some of the kiosk controls can be generated at a remote location, such as a user's mobile device or a server system, and can be provided at block 534 to the phototherapy kiosk. Generating kiosk controls can include applying an algorithm that takes user biometrics, user selections, third-party selections, or phototherapy kiosk usage history for the user, and generates a base set of treatment parameters. These treatment parameters can be updated based on the user's erythema factors. These treatment parameters can also be updated based on telemetry measurements taken as a session progresses. The treatment parameters can be converted into controls that can be implemented by a phototherapy kiosk. Additional details regarding determining treatment parameters and generating phototherapy kiosk controls are discussed below in relation to FIG. 6. In some implementations, determining treatment parameters can include a usability check which can result in blocking of treatment. If this occurs, process 500 can skip to block 542.

At block 536, process 500 can operate the phototherapy kiosk based on the kiosk controls generated at block 534. Kiosk controls can be signals that actuate various components of the phototherapy kiosk. Kiosk controls based on treatment parameters can operate one or more radiation emitting devices to deliver a logic-controlled dose of radiation to part or the entire skin surface of a user. Kiosk controls based on treatment parameters can control a radiation intensity setting, one or more timers for the session, timers for radiation at various settings, applications of wavelength filtering, or light source selection. Kiosk controls can also operate a door based on a session state. Kiosk controls can also actuate other environment components of the phototherapy kiosk, such as lighting, temperature controls, or entertainment components (e.g. a screen and/or speakers). Kiosk controls can also cause instructions or notifications to be provided to a user, e.g. by accessing content for the instructions or notifications and providing them through an output, such as a screen, speaker, or haptic feedback device.

At block 538, process 500 can take telemetry measurements in relation to an in-progress treatment session. Telemetry measurements can include temperature measurements, motion measurements, electric current measurements, iridescence measurements, or monitoring of specific devices. Temperature measurements can include measurements of temperature in a treatment chamber of the phototherapy kiosk, in a lamp chamber of the phototherapy kiosk, in a ballast chamber of the phototherapy kiosk, or in an onboard computer housing area of the phototherapy kiosk. Motion measurements can include measurements of user activity based on signals from one or more of an infrared device, ultrasound device, pressure pad, contact switch, current resistance measurement device, visible light (e.g. from a camera), or RF measurement device. Irradiance can be measured based on reading from a spectroradiometer. Irradiance can be measured for a user's skin generally or for a specific treatment location. Examples of specific device monitoring include lamp failure, power failure, door status, etc. Telemetry measurements can be used for machine status or performance monitoring, user treatment analytics and updates, or emergency detection.

At block 540, process 500 can determine whether the current session has ended. This can be based on the expiration of the timer, a determination to block treatment (e.g. at block 612), a change in machine state (e.g. open-door, emergency detected, etc. that causes the UV radiation units to automatically terminate emission of UV radiation), a detected change in a user state (e.g. iridescence level, motion activity, or other telemetry data), or a user selection to end the session. A "Stop" button or command can prompt a dialog box or audio message to confirm intent to terminate the current treatment early or can turn off the treatment light panel immediately. In some implementations, the phototherapy kiosk can include a countdown timer displaying the current time remaining in the active treatment. When the countdown timer reaches zero, the treatment has ended. When the session has ended, a treatment light source can turn off automatically. When the session has ended, process 500 continues to block 542. If the session has not ended, process 500 returns to block 534 to determine whether any updates are needed to the kiosk controls.

At block 542, process 500 can generate result data following a completed treatment session. Some of the result data can be based on user responses to post-session questions. A Treatment Response page can include questions that ask if the user experienced a skin color change (also referred to as erythema, pinkness, sun burn, tanning, etc.) resulting from the last phototherapy kiosk treatment. A response to the color change question can cause presentation of additional questions to allow the system to characterize a skin response using a Skin Change page or a Discomfort page. A phototherapy kiosk treatment should not result in any discomfort if treatment parameters were correct. Depending on how the user answers discomfort questions, they can go to a Pain Rating page or a Dose Adjustment page. Questions following a treatment session can also allow a user to report their mood following the session, a sense of physical or mental energy following the session, ratings for environment of the treatment (e.g. sound volume, temperature, lighting level, lighting color), or entertainment rating. The phototherapy kiosk can provide the post session questions through an integrated audio or visual input output system or through an interface provided on the user's mobile device.

Result data can also include information logged by the phototherapy kiosk during the session. For example, the result data can include treatment parameters used throughout the session, user settings of environment controls, recorded telemetry data, changes in phototherapy kiosk system state throughout the session, total treatment time, user preparation time (door closed through treatment start), exit time (session complete to door open), etc.

In some implementations, the phototherapy kiosk can transmit the result data to an external system such as a central server system or to the user's personal computing system. The result data can be used to generate various analytics and algorithms for the particular user. The result data can also be associated with the user's skin type and can be used, in conjunction with result data from other users, to generate various analytics and algorithms for user skin types. For example, positive or negative identifications of erythema or discomfort can be paired with skin types to train a machine learning engine to select treatment parameters for skin types (and/or other user biometrics or telemetry data). As another example, the result data can inform establishing future treatment sessions for a particular user or treatment parameters for such sessions, such as length of time until next session or duration or intensity of radiation to use in one or more following sessions. In some implementations, result data can include a logged event if a current user opens the door, speaks a stop command, activates a termination control, or otherwise stops treatment prior to completion of the scheduled logic-controlled dose of radiation. When the system determines dosage for a subsequent treatment session for the user, the radiation intensity or duration can be decreased based on the logged result data indicating the user terminated one or more previous sessions before completion of the scheduled logic-controlled dose of radiation. Process 500 then continues to block 544, where it ends.

Figure 6:
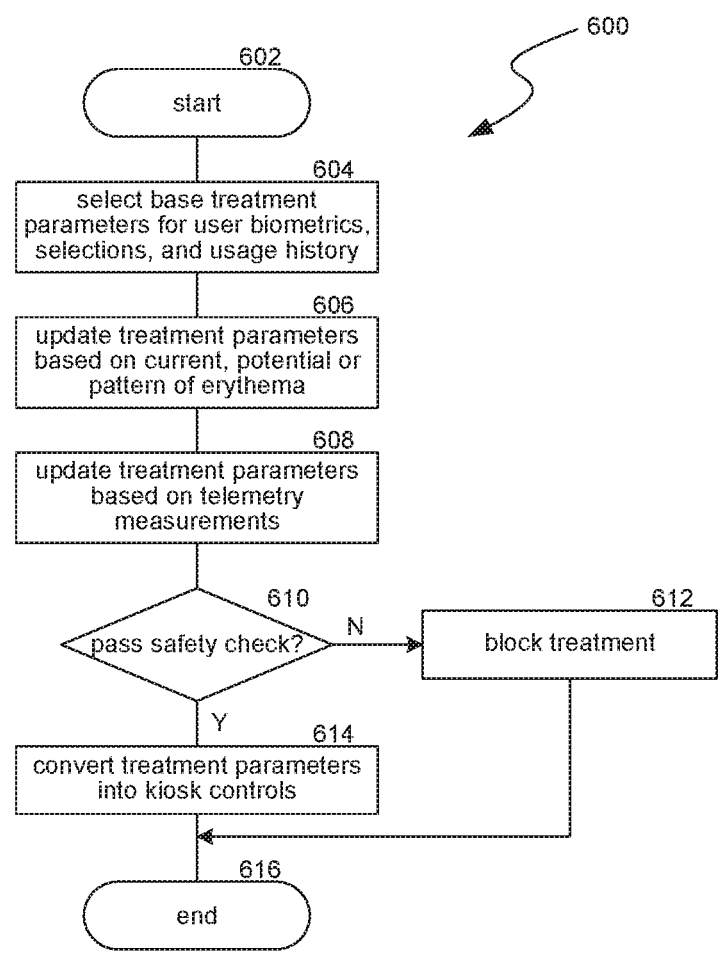
FIG. 6 is a flow diagram illustrating a process used in some implementations for selecting treatment parameters and converting the treatment parameters into kiosk controls.

FIG. 6 is a flow diagram illustrating a process 600 used in some implementations for selecting treatment parameters and converting the treatment parameters into kiosk controls. In some implementations, process 600 can be called from block 534 of process 500. In various implementations, process 600 can be performed by the phototherapy kiosk, a personal computing system of the user, or a server system administrating one or more phototherapy kiosks. Process 600 begins at block 602 and continues to block 604.

At block 604, process 600 can select a set of base treatment parameters for the current treatment session. The base parameters can be responsive to user data obtained at one of block 528-532, such as user biometrics, selections from a user or medical professional, or the user's history of use with the phototherapy system. Treatment parameters can define one or more of treatment dose (time and/or intensity), wavelength filtering, light source selection, or dose escalation. Treatment parameters can be determined by applying a dosing algorithm to user specifics and parameters defined for the current treatment session. For example, user specifics and parameters can be identified based on irradiance degradation over time for the user; the users skin type, the user's age, gender, height, BMI, or other biometrics; identified previous exposure to radiation of the user; treatment history of the user; identified medication the user is taking; or identified serum bio-markers of the user (e.g. T-cell counts, 25 (OHD), Parathyroid hormone, Calcium). Additional details on applying an algorithm to determine treatment parameters are described in U.S. Patent application 62/599, 252 titled "DYNAMIC DOSING SYSTEM FOR SELF-CARE PHOTOTHERAPY" filed on Dec. 15, 2017 and incorporated herein by reference. In some implementations, process 600 can be repeated one or more times throughout a treatment session, in which case the base treatment parameters can be determined from a previous execution of process 600.

At block 606, process 600 can update the base treatment parameters based on the user's current, potential, or an identified pattern of erythema. Erythema is reddening of the skin induced by increased blood flow to the capillaries in the lower skin layers and is a common consequence of UVR exposure and the hallmark of sunburn. The lowest dose of radiation necessary to produce minimal perceptible erythema with well-defined borders is considered 1 Minimal Erythemal Dose (MED). Increased melanin provides photoprotection, decreasing sun sensitivity, and directly correlating with higher UVR dosage requirements to produce erythema. There is a stepwise increase in the average MED between skin types. If a user indicates a current erythema level, treatment parameters can be adjusted. For example, an adjustment amount can be determined by taking a numerical representation of the user's skin type minus an erythema scale value. If a user indicates a particular susceptibility to erythema, the treatment parameters can be scaled back to lower radiation levels. Similarly, if a pattern of erythema has been determined, e.g. based on post-session questions from a series of previous sessions, the treatment parameters can be scaled back to lower radiation levels.

In some implementations, the erythema adjustments can be implemented using a Dose Adjustment page which is displayed upon determining a user's current, potential, or an identified pattern of erythema. The Dose Adjustment page can display the user's reported skin color change and discomfort response to previous phototherapy kiosk treatment. Information about future treatment adjustments can be displayed on this page. In some implementations, an ultraviolet B (UVB) phototherapy kiosk treatment should not result in any lasting skin color change or discomfort if the dosage is correct. Answers to questions about a previous treatment response can allow the system to adjust dosage for future treatments, if needed, to prevent lasting skin color change or discomfort. Some responses to post-treatment questions can result in blocking of treatment, as discussed in blocks 610-612.

At block 608, if a treatment is in progress and telemetry measurements have been taken, process 600 can further update the treatment parameters based on the telemetry measurements. Process 600 can adjust treatment parameters up or down based on identified user motion data, iridescence levels, or for certain usability conditions. For example, based on telemetry data, the process 600 can determine if there is a user emergency if the door is closed, no user exit has occurred, and no motion is detected within the phototherapy kiosk; if treatment in progress and there has been no motion within a set amount of time; or if treatment has completed and the door has not been opened or unlocked after a set amount of time. User activity or motion measurements can further be used to trigger: instructions for use, notifications (e.g. call 911, mobile notification, text message, phone call, external display), lighting changes, door lock or unlocking, start/pause/stop treatment, or playing a sound. In some implementations, spectral irradiance measurements in the telemetry measurements can be used to adjust treatment parameters. For example, spectral irradiance measurements can be compared to a standard baseline measurement, to a previous treatment of the user, across a current treatment, or to a measurement from immediately before the current treatment. Depending on the comparison, treatment parameters can be adjusted. For example, a change, in a spectral irradiance measurement from before the session to the current level during the session, that is above a threshold, can cause a corresponding reduction in treatment parameters controlling dosage (e.g. reducing intensity or duration). In some implementations, an irradiance measure can be determined by applying a function that takes a measure of power input to UV radiation units and provides an irradiance value. This function can be based on tests that measure power input and correlated irradiance. In some cases, these tests can be performed on one or more phototherapy kiosks with the results being used to define a function for other phototherapy kiosks. In other cases, these tests can be performed on a particular phototherapy kiosk with the results being used to define a function specific to that particular phototherapy kiosk.

At block 610, process 600 can perform various usability checks. Usability checks can identify some hazards for the phototherapy kiosk user or others in the vicinity of the phototherapy kiosk or can identify situations that may damage the phototherapy kiosk. The frequency for phototherapy treatment should be regulated to prevent overexposure. Different intervals of time between treatments may be needed depending on the indication, regulatory (FDA, Health Canada, etc.) restrictions and treatment protocol. For example, UVB phototherapy for psoriasis treatment usually consists of three exposures per week for at least three months and then a frequency of once every two weeks is required for maintenance. For endogenous vitamin D, thermal isomerization of pre-vitamin D3 to vitamin D3 takes three days to complete and photodegradation of cutaneous vitamin D3 prior circulation transfer means repeated treatments within this three-day window would be counterproductive. Additionally, the cutaneous translocation of vitamin D3 to circulation can take seven or more days to complete. Therefore, treatments can be more frequent (every three days) at the beginning of endogenous vitamin D therapy to address an acute need and less frequent (every seven days) after a month to favor efficiency of conversion for maintenance dosing. The phototherapy kiosk can prevent user's from initiating a treatment session based on these types of guidelines to insure phototherapy kiosk usability. In some implementations, a usability check can pass or fail based on user question responses (e.g. in FIG. 7). For example, if a user indicates they are taking certain medications, the usability check can fail until a medical professional approves the treatment.

In some implementations, there may be no usability concerns when a user initiates a session, but the system can detect a usability concern during the session, causing failure of a subsequent usability check. For example, the phototherapy kiosk can monitor the status of a door and block treatment immediately (or after a short period of time e.g. 1-10 seconds) if the door is opened. In this case, a Close Door page can be displayed. An audio message such as "close the door" or "keep the device closed" can be played with or instead of this page. Once the door is closed, the phototherapy kiosk can automatically proceed with the treatment process. Additional usability concerns can be identified based on changes in measured user iridescence levels or lack of user movement. If a usability check fails, process 600 can continue to block 612, otherwise process 600 can continue to block 614.

At block 612, a usability check has failed and kiosk controls are generated to block treatment. Failing a usability check can cause the phototherapy kiosk to be disabled or can prevent the user from using this or other phototherapy kiosks for a set amount of time or until authorized by a medical professional or phototherapy kiosk administrator. This can be accomplished by generating kiosk controls corresponding to the failed usability check. In some implementations, the kiosk controls can be for a display or auditory function of the phototherapy kiosk to provide a user notification about the usability concern. In some cases, the kiosk controls can turn off the radiation emission system of the phototherapy kiosk. In some cases, the kiosk control can adjust environment settings of the phototherapy kiosk, such as by adjusting the volume or enabling lights.

At block 614, when the usability checks have passed, the treatment parameters determined through blocks 604-608 can be converted into specific kiosk controls for the phototherapy kiosk. Treatment parameters specify treatment specifics such as radiation duration, intensity, wavelength filters, and skin areas to treat. Kiosk controls are the instructions to the specific devices embodied in the phototherapy kiosk that implement these parameters. For example, a treatment parameter specifying treatment duration can be converted into a timer setting on one or more radiation lamps while an intensity treatment parameter can be converted into a kiosk control specifying which lamps to enable or amounts of power to supply them with. A set of mappings, each starting with one or more treatment parameters and ending with one or more kiosk controls can be used to enact this conversion. In some implementations, kiosk controls can include display or audio notifications. For example, when a lamp timer is set, a corresponding countdown can be displayed. In some implementations, the kiosk controls can lock or unlock a phototherapy kiosk door. In some implementations, kiosk controls can provide a signal outside the phototherapy kiosk, such as to contact a technician or phototherapy kiosk monitoring station.

Process 600 can provide the kiosk controls generated at block 612 or 614, and continue to block 616, where it ends.

The following is a non-exhaustive list of additional examples of the disclosed technology.

1. A method for operating a phototherapy system, the method comprising:

obtaining one or more data sources comprising one or more of: user account information, a remote payload, user input, measurements by a phototherapy kiosk, or any combination thereof;

determining base treatment parameters based on the data sources, wherein the base treatment parameters specify one or more of: radiation duration, radiation intensity, wavelength filters, radiation dose escalation, skin areas to treat, or any combination thereof;

applying one or more mappings that map treatment parameters to kiosk controls; and causing the kiosk controls to be applied at the phototherapy kiosk, wherein applying at least some of the kiosk controls comprises operating one or more UV radiation units.

2. The method of example 1 further comprising updating the base treatment parameters based on one or more of:
a measured level of erythema in a user during a current treatment session;
an identified potential for erythema in the user based on a user skin characteristic;
an identified pattern of erythema in the user across previous treatment sessions; or
any combination thereof.

3. The method of example 1 or 2 further comprising updating the base treatment parameters by applying an adjustment amount determined by taking a numerical representation of a user's skin type minus an erythema scale value.

4. The method of any of examples 1-3 further comprising updating the base treatment parameters by applying an adjustment amount that is based on a user-specified susceptibility to erythema.

5. The method of any of examples 1-4,
wherein the phototherapy system includes a telemetry capture system comprising a spectroradiometer;
wherein the telemetry capture system determines, at least in part, an irradiance measure for a user; and
wherein the method further comprises updating previous treatment parameters based on the irradiance measure.

6. The method of any of examples 1-5,
wherein the irradiance measure is determined as a comparison value between a current irradiance reading for the user compared to one or more of:
a baseline irradiance reading,
an irradiance reading from a previous treatment of the user, or
an irradiance reading from an earlier point in a current treatment of the user; and
wherein updating the previous treatment parameters based on the irradiance measure comprises determining whether the irradiance measure is above a threshold and, if so, reducing a radiation duration or a radiation intensity specified in the previous treatment parameters.

7. The method of any of examples 1-6,
wherein the one or more data sources include identifications of one or more medications for a user; and
wherein the method further comprises updating the base treatment parameters by applying an adjustment amount based on the identifications of one or more medications.

8. The method of any of examples 1-7, wherein the one or more data sources include the user account information and wherein the user account information was entered via a personal computing device of a user and comprises information specifying one or more of: skin type, age, gender, phototherapy treatment preferences, or any combination thereof.

9. The method of any of examples 1-8, wherein the one or more data sources include the remote payload, wherein a least a part of the remote payload was generated by a medical professional and includes one or more of: a skin type designation, UV dosing instructions, treatment history, or any combination thereof.

10. The method of any of examples 1-9,
wherein the phototherapy system includes a light capture device; and
wherein obtaining at least one of the one or more data sources includes the light capture device reading a barcode or QR code displayed on a screen of a mobile device.

11. The method of any of examples 1-10,
wherein the phototherapy system includes a door with a sensor arrangement that provides a status of the door; and
wherein the method further comprises determining that the status of the door indicates the door has been at least partially opened and, in response, automatically terminating emission of UV radiation from the one or more UV radiation units.

12. The method of example 11 further comprising:
logging result data, in association with a current user, upon the determining that the status of the door indicates the door has been at least partially opened; and
in a subsequent treatment session for the user, delivering an adjusted logic-controlled dose of radiation that is at least partially based on the logged result data.

13. The method of any of examples 1-12 further comprising, in response to completing a treatment session for the current user, storing result data comprising one or more of:
an indication of change in user skin color during the treatment session;
treatment parameters used during the treatment session;
user settings of environment controls during the treatment session; or
any combination thereof.

14. The method of example 13,
wherein the result data comprises training data including skin types paired with positive or negative identifications of erythema or discomfort experienced by the current user during the treatment session; and
wherein the training data is used to in conjunction with training data from other users to train a machine learning engine to select treatment parameters for given skin types.

15. The method of example 13 or 14, wherein the result data is used as a basis for automatically selecting treatment parameters for one or more future treatment sessions for the current user.

16. A computer-readable storage medium storing instructions that, when executed by a computing system, cause the computing system to perform operations comprising:
obtaining one or more data sources comprising information for operating a phototherapy kiosk;
determining treatment parameters based on the data sources, wherein the base treatment parameters specify one or more of: radiation duration, radiation intensity, wavelength filters, radiation dose escalation, skin areas to treat, or any combination thereof;
determining kiosk controls based on the treatment parameters; and causing the kiosk controls to be implemented, wherein implementing at least some of the kiosk controls comprises operating one or more UV radiation units of the phototherapy kiosk.

17. The computer-readable storage medium of example 16, wherein the operations further comprise updating the treatment parameters based on one or more of:
   a measured level of erythema in a user during a current treatment session;
   an identified potential for erythema in the user based on a user skin characteristic;
   an identified pattern of erythema in the user across previous treatment sessions; or
   any combination thereof.

18. The computer-readable storage medium of example 16 or 17, wherein the operations further comprise updating the treatment parameters by applying an adjustment amount determined by taking a numerical representation of a user's skin type minus an erythema scale value.

19. The computer-readable storage medium of any of examples 16-18, wherein the operations further comprise updating the treatment parameters by applying an adjustment amount that is based on a user-specified susceptibility to erythema.

20. The computer-readable storage medium of any of examples 16-19,
   wherein the computing system is coupled to a telemetry capture system comprising a spectroradiometer;
   wherein the telemetry capture system determines, at least in part, an irradiance measure for a user; and
   wherein the operations further comprise updating previous treatment parameters based on the irradiance measure.

21. The computer-readable storage medium of example 20,
   wherein the irradiance measure is determined as a comparison value between a current irradiance reading for the user compared to one or more of:
      a baseline irradiance reading,
      an irradiance reading from a previous treatment of the user, or
      an irradiance reading from an earlier point in a current treatment of the user; and
   wherein updating the previous treatment parameters based on the irradiance measure comprises determining whether the irradiance measure is above a threshold and, if so, reducing a radiation duration or a radiation intensity specified in the previous treatment parameters.

22. The computer-readable storage medium of any of examples 16-21,
   wherein the one or more data sources include identifications of one or more medications for the user; and
   wherein the operations further comprise updating the treatment parameters by applying an adjustment amount based on the identifications of one or more medications.

23. The computer-readable storage medium of any of examples 16-22, wherein the one or more data sources include user account information entered via a personal computing device and comprises information specifying one or more of: skin type, age, gender, phototherapy treatment preferences, or any combination thereof.

24. The computer-readable storage medium of any of examples 16-23, wherein the one or more data sources include a remote payload, wherein a least a part of the remote payload was generated by a medical professional and includes one or more of: a skin type designation, UV dosing instructions, treatment history, or any combination thereof.

25. The computer-readable storage medium of any of examples 16-24,
   wherein the computing system is coupled to a light capture device; and
   wherein obtaining at least one of the one or more data sources includes the light capture device reading a barcode or QR code displayed on a screen of a mobile device.

26. The computer-readable storage medium of any of examples 16-25,
   wherein the computing system is coupled to a door with a sensor arrangement that provides a status of the door to the computing system; and
   wherein the operations further comprise determining that the status of the door indicates the door has been at least partially opened and, in response, automatically terminating emission of UV radiation from the one or more UV radiation units.

27. The computer-readable storage medium of example 26, wherein the operations further comprise:
   logging result data, in association with a current user, upon the determining that the status of the door indicates the door has been at least partially opened; and
   in a subsequent treatment session for a current user, delivering an adjusted logic-controlled dose of radiation that is at least partially based on the logged result data.

28. The computer-readable storage medium of any of examples 16-27, wherein the operations further comprise, in response to completing a treatment session for the current user, storing result data comprising one or more of:
   an indication of change in user skin color during the treatment session;
   treatment parameters used during the treatment session;
   user settings of environment controls during the treatment session; or
   any combination thereof.

29. The computer-readable storage medium of example 28,
   wherein the result data comprises training data including skin types paired with positive or negative identifications of erythema or discomfort experienced by the current user during the treatment session; and
   wherein the training data is used to in conjunction with training data from other users to train a machine learning engine to select treatment parameters for given skin types.

30. The computer-readable storage medium of example 28 or 29, wherein the result data is used as a basis for automatically selecting treatment parameters for one or more future treatment sessions for the current user.

31. A phototherapy kiosk that is operated based on kiosk controls, the phototherapy kiosk comprising:
   a phototherapeutic assembly comprising one or more UV radiation units configured to emit UV radiation;
   one or more input interfaces configured to obtain one or more data sources comprising one or more of: user account information, a remote payload, user input, measurements by the phototherapy kiosk, one or more of the kiosk controls, or any combination thereof; and
   a phototherapy kiosk controller configured to implement the kiosk controls based on the one or more data sources, wherein implementing at least some of the kiosk controls comprises operating at least one of the one or more UV radiation units to deliver a logic-controlled dose of radiation to at least part of a user's skin surface.

32. The phototherapy kiosk of example 31,
wherein the phototherapy kiosk has one or more internal surfaces that form an enclosure;
wherein the phototherapeutic includes a treatment light panel facing into the enclosure to emit the UV radiation into the enclosure; and
wherein the phototherapy kiosk further comprises:
a first user interface mounted on an external surface of the phototherapy kiosk facing an area external to the enclosure;
a second user interface mounted on one of the internal surfaces facing into the enclosure; and
a door that, when open, provides access for a user to enter or exit the enclosure and that, when closed, prevents at least part of the UV radiation from exiting the enclosure during the logic-controlled dose of radiation.

33. The phototherapy kiosk of example 31 or 32, wherein the kiosk controls are generated by:
determining base treatment parameters based on the data sources, wherein the base treatment parameters specify one or more of: radiation duration, radiation intensity, wavelength filters, radiation dose escalation, skin areas to treat, or any combination thereof; and
applying one or more mappings that map at least one treatment parameter to at least one kiosk control.

34. The phototherapy kiosk of example 33, wherein generating the kiosk controls includes updating the base treatment parameters based on one or more of:
a measured level of erythema in the user during a current treatment session;
an identified potential for erythema in the user based on a user skin characteristic;
an identified pattern of erythema in the user across previous treatment sessions; or
any combination thereof.

35. The phototherapy kiosk of example 33 or 34, wherein generating the kiosk controls includes updating the base treatment parameters by applying an adjustment amount determined by taking a numerical representation of the user's skin type minus an erythema scale value.

36. The phototherapy kiosk of any of examples 33-35, wherein generating the kiosk controls includes updating the base treatment parameters by applying an adjustment amount that is based on a user-specified susceptibility to erythema.

37. The phototherapy kiosk of any of examples 33-36,
wherein the one or more input interfaces includes a telemetry capture system comprising a spectroradiometer;
wherein the telemetry capture system determines, at least in part, an irradiance measure for the user; and
wherein generating the kiosk controls includes updating previous treatment parameters based on the irradiance measure.

38. The phototherapy kiosk of example 37,
wherein the irradiance measure is determined as a comparison value between a current irradiance reading for the user compared to one or more of:
a baseline irradiance reading,
an irradiance reading from a previous treatment of the user, or
an irradiance reading from an earlier point in a current treatment of the user; and
wherein updating the previous treatment parameters based on the irradiance measure comprises determining whether the irradiance measure is above a threshold and, if so, reducing a radiation duration or a radiation intensity specified in the previous treatment parameters.

39. The phototherapy kiosk of any of examples 31-38,
wherein the one or more data sources include identifications of one or more medications for the user; and
wherein generating the kiosk controls includes updating the base treatment parameters by applying an adjustment amount based on the identifications of one or more medications.

40. The phototherapy kiosk of any of examples 31-39, wherein the one or more data sources include the user account information and wherein the user account information was entered via a personal computing device of the user and comprises information specifying one or more of: skin type, age, gender, phototherapy treatment preferences, or any combination thereof.

41. The phototherapy kiosk of any of examples 31-40, wherein the one or more data sources include the remote payload, wherein a least a part of the remote payload was generated by a medical professional and includes one or more of: a skin type designation, UV dosing instructions, treatment history, or any combination thereof.

42. The phototherapy kiosk of any of examples 31-41,
wherein at least one of the one or more input interfaces includes a light capture device; and
wherein obtaining at least one of the one or more data sources includes the light capture device reading a barcode or QR code displayed on a screen of a mobile device.

43. The phototherapy kiosk of any of examples 31-42, further comprising:
a door with a sensor arrangement that provides a status of the door to the phototherapy kiosk controller;
wherein implementing the kiosk controls by the phototherapy kiosk controller further includes determining that the status of the door indicates the door has been at least partially opened and, in response, automatically terminating emission of UV radiation from the one or more UV radiation units.

44. The phototherapy kiosk of example 43,
wherein the phototherapy kiosk controller is further configured to log result data, in association with a current user, upon the determining that the status of the door indicates the door has been at least partially opened during the logic-controlled dose of radiation; and
wherein the phototherapy kiosk controller is further configured to, in a subsequent treatment session for the current user, deliver an adjusted logic-controlled dose of radiation that is at least partially based on the logged result data.

45. The phototherapy kiosk of any of examples 31-44, wherein the phototherapy kiosk controller is further configured to, in response to completing a treatment session in which the dose of radiation was administered, storing result data comprising one or more of:
an indication of change in user skin color during the treatment session;
treatment parameters used during the treatment session;
user settings of environment controls during the treatment session; or
any combination thereof.

46. The phototherapy kiosk of example 45, wherein the result data comprises training data including skin types paired with positive or negative identifications of erythema or discomfort experienced by the user during the treatment session; and wherein the training data is used to in conjunction with training data from other users to train a machine learning engine to select treatment parameters for given skin types.

47. The phototherapy kiosk of example 45 or 46, wherein the result data is used as a basis for automatically selecting treatment parameters for one or more future treatment sessions for the user.

Several implementations of the disclosed technology are described above in reference to the figures. The computing devices on which the described technology may be implemented can include one or more central processing units, memory, input devices (e.g., keyboard and pointing devices), output devices (e.g., display devices), storage devices (e.g., disk drives), and network devices (e.g., network interfaces). The memory and storage devices are computer-readable storage media that can store instructions that implement at least portions of the described technology. In addition, the data structures and message structures can be stored or transmitted via a data transmission medium, such as a signal on a communications link. Various communications links can be used, such as the Internet, a local area network, a wide area network, or a point-to-point dial-up connection. Thus, computer-readable media can comprise computer-readable storage media (e.g., "non-transitory" media) and computer-readable transmission media.

Reference in this specification to "implementations" (e.g. "some implementations," "various implementations," "one implementation," "an implementation," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle specified number of items, or that an item under comparison has a value within a middle specified percentage range. Relative terms, such as "high" or "unimportant," when not otherwise defined, can be understood as assigning a value and determining how that value compares to an established threshold. For example, the phrase "selecting a fast connection" can be understood to mean selecting a connection that has a value assigned corresponding to its connection speed that is above a threshold.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

We claim:

1. A method for operating a phototherapy system, the method comprising:
    obtaining one or more data sources comprising one or more of: user account information, a remote payload, user input, measurements by a phototherapy kiosk, or any combination thereof;
    determining base treatment parameters based on the data sources, wherein the base treatment parameters specify one or more of: radiation duration, radiation intensity, wavelength filters, radiation dose escalation, skin areas to treat, or any combination thereof;
    applying one or more mappings that map treatment parameters to first kiosk controls; and
    performing a usability check to detect if a hazard exists to a user of the phototherapy kiosk,
    wherein:
        in response to a hazard not being detected, the method further includes causing the first kiosk controls to be applied at the phototherapy kiosk, wherein applying at least some of the first kiosk controls comprises operating one or more UV radiation units, and
        in response to a hazard being detected, the method further includes generating second kiosk controls to block the phototherapy kiosk from providing any radiation to the user of the phototherapy kiosk.

2. The method of claim 1 further comprising updating the base treatment parameters by applying an adjustment amount based on:
    a numerical representation of a user's skin type minus an erythema scale value; or
    a user-specified susceptibility to erythema.

3. The method of claim 1,
    wherein the one or more data sources include identifications of one or more medications for a user; and
    wherein the method further comprises updating the base treatment parameters by applying an adjustment amount based on the identifications of one or more medications.

4. A computer-readable storage medium storing instructions that, when executed by a computing system, cause the computing system to perform operations comprising:
- obtaining one or more data sources comprising information for operating a phototherapy kiosk;
- determining treatment parameters based on the data sources, wherein the base treatment parameters specify one or more of: radiation duration, radiation intensity, wavelength filters, radiation dose escalation, skin areas to treat or any combination thereof;
- determining first kiosk controls based on the treatment parameters; and
- performing a usability check to detect if a hazard exists to a user of the phototherapy kiosk,
  - wherein:
    - in response to a hazard not being detected, causing the first kiosk controls to be implemented, wherein implementing at least some of the first kiosk controls comprises operating one or more UV radiation units of the phototherapy kiosk, and
    - in response to a hazard being detected, generating second kiosk controls to block the phototherapy kiosk from providing any radiation to the user of the phototherapy kiosk until authorized by an administrator of the phototherapy kiosk.

5. The computer-readable storage medium of claim 4,
- wherein the one or more data sources include identifications of one or more medications for the user; and
- wherein the operations further comprise updating the treatment parameters by applying an adjustment amount based on the identifications of one or more medications.

6. The computer-readable storage medium of claim 4, wherein the one or more data sources include a remote payload, wherein a least a part of the remote payload was generated by a medical professional and includes one or more of: a skin type designation, UV dosing instructions, treatment history, or any combination thereof.

7. The computer-readable storage medium of claim 4, wherein the operations further comprise, in response to completing a treatment session for the current user, storing result data comprising one or more of:
- an indication of change in user skin color during the treatment session;
- treatment parameters used during the treatment session;
- user settings of environment controls during the treatment session; or
- any combination thereof.

8. The computer-readable storage medium of claim 7, wherein the result data is used as a basis for automatically selecting treatment parameters for one or more future treatment sessions for the current user.

9. A phototherapy kiosk that is operated based on kiosk controls, the phototherapy kiosk comprising:
- a phototherapeutic assembly comprising one or more UV radiation units configured to emit UV radiation;
- one or more input interfaces configured to obtain one or more data sources comprising one or more of: user account information, a remote payload, user input, measurements by the phototherapy kiosk, one or more of the kiosk controls, or any combination thereof; and
- a phototherapy kiosk controller configured to implement the kiosk controls based on the one or more data sources, wherein implementing at least some of the kiosk controls comprises performing a usability check to detect if a hazard exists to a user of the phototherapy kiosk and, wherein:
  - in response to a hazard not being detected, implementing at least some of the kiosk controls further comprises operating at least one of the one or more UV radiation units to deliver a logic-controlled dose of radiation to at least part of a user's skin surface, and
  - in response to a hazard being detected, implementing at least some of the kiosk controls further comprises blocking the phototherapy kiosk from operating for at least a predetermined amount of time.

10. The phototherapy kiosk of claim 9,
- wherein the phototherapy kiosk has one or more internal surfaces that form an enclosure;
- wherein the phototherapeutic includes a treatment light panel facing into the enclosure to emit the UV radiation into the enclosure; and
- wherein the phototherapy kiosk further comprises:
  - a first user interface mounted on an external surface of the phototherapy kiosk facing an area external to the enclosure;
  - a second user interface mounted on one of the internal surfaces facing into the enclosure; and
  - a door that, when open, provides access for a user to enter or exit the enclosure and that, when closed, prevents at least part of the UV radiation from exiting the enclosure during the logic-controlled dose of radiation.

11. The phototherapy kiosk of claim 9, wherein the kiosk controls are generated by:
- determining base treatment parameters based on the data sources, wherein the base treatment parameters specify one or more of: radiation duration, radiation intensity, wavelength filters, radiation dose escalation, skin areas to treat, or any combination thereof; and
- applying one or more mappings that map at least one treatment parameter to at least one kiosk control.

12. The phototherapy kiosk of claim 11, wherein generating the kiosk controls includes updating the base treatment parameters based on one or more of:
- a measured level of erythema in the user during a current treatment session;
- an identified potential for erythema in the user based on a user skin characteristic;
- an identified pattern of erythema in the user across previous treatment sessions; or
- any combination thereof.

13. The phototherapy kiosk of claim 11, wherein generating the kiosk controls includes updating the base treatment parameters by applying an adjustment amount determined by taking a numerical representation of the user's skin type minus an erythema scale value.

14. The phototherapy kiosk of claim 11, wherein generating the kiosk controls includes updating the base treatment parameters by applying an adjustment amount that is based on a user-specified susceptibility to erythema.

15. The phototherapy kiosk of claim 11,
- wherein the one or more input interfaces includes a telemetry capture system comprising a spectroradiometer;
- wherein the telemetry capture system determines, at least in part, an irradiance measure for the user; and
- wherein generating the kiosk controls includes updating previous treatment parameters based on the irradiance measure.

16. The phototherapy kiosk of claim 15,
- wherein the irradiance measure is determined as a comparison value between a current irradiance reading for the user compared to one or more of:

a baseline irradiance reading,
an irradiance reading from a previous treatment of the user, or
an irradiance reading from an earlier point in a current treatment of the user; and
wherein updating the previous treatment parameters based on the irradiance measure comprises determining whether the irradiance measure is above a threshold and, if so, reducing a radiation duration or a radiation intensity specified in the previous treatment parameters.

17. The phototherapy kiosk of claim 9, wherein the one or more data sources include the user account information and wherein the user account information was entered via a personal computing device of the user and comprises information specifying one or more of: skin type, age, gender, phototherapy treatment preferences, or any combination thereof.

18. The phototherapy kiosk of claim 9,
wherein at least one of the one or more input interfaces includes a light capture device; and
wherein obtaining at least one of the one or more data sources includes the light capture device reading a barcode or QR code displayed on a screen of a mobile device.

19. The phototherapy kiosk of claim 9, wherein the phototherapy kiosk controller is further configured to, in response to completing a treatment session in which the dose of radiation was administered, storing result data comprising one or more of:

an indication of change in user skin color during the treatment session;

treatment parameters used during the treatment session;

user settings of environment controls during the treatment session; or any combination thereof.

20. The phototherapy kiosk of claim 19,
wherein the result data comprises training data including skin types paired with positive or negative identifications of erythema or discomfort experienced by the user during the treatment session; and
wherein the training data is used to in conjunction with training data from other users to train a machine learning engine to select treatment parameters for given skin types.

* * * * *